(12) United States Patent
Shahbaz

(10) Patent No.: US 6,908,741 B1
(45) Date of Patent: Jun. 21, 2005

(54) METHODS TO IDENTIFY COMPOUNDS THAT MODULATE RAGE

(75) Inventor: Manouchehr M. Shahbaz, Oak Ridge, NC (US)

(73) Assignee: TransTech Pharma, Inc., High Point, NC (US)

( * ) Notice: Subject to any disclaimer, the term of this patent is extended or adjusted under 35 U.S.C. 154(b) by 353 days.

(21) Appl. No.: 09/799,152

(22) Filed: Mar. 5, 2001

Related U.S. Application Data

(60) Provisional application No. 60/207,342, filed on May 30, 2000.

(51) Int. Cl.$^7$ .......................... G01N 33/53; C12Q 1/04; C12N 5/06
(52) U.S. Cl. ................. 435/7.92; 435/7.1; 435/35; 530/350
(58) Field of Search ................ 435/7.92, 7.1, 435/35; 436/501; 530/350

(56) References Cited

U.S. PATENT DOCUMENTS

| | | | |
|---|---|---|---|
| 4,166,452 | A | 9/1979 | Generales, Jr. |
| 4,265,874 | A | 5/1981 | Bonsen et al. |
| 4,356,108 | A | 10/1982 | Schwab et al. |
| 4,873,313 | A | 10/1989 | Crawford et al. |
| 5,202,424 | A | 4/1993 | Vlassara et al. |
| 5,585,344 | A | 12/1996 | Vlassara et al. |
| 5,688,653 | A | 11/1997 | Ulrich et al. |
| 5,864,018 | A | 1/1999 | Morser et al. |
| 5,939,536 | A | 8/1999 | Gaugler et al. |
| 6,100,098 | A | 8/2000 | Newkirk |
| 6,555,340 | B1 * | 4/2003 | Schmidt et al. |

FOREIGN PATENT DOCUMENTS

| | | |
|---|---|---|
| WO | WO 97/26913 | 7/1997 |
| WO | WO 97/39121 | 10/1997 |
| WO | WO 97/39125 | 10/1997 |
| WO | WO 98/22138 | 5/1998 |
| WO | WO 99/07402 | 2/1999 |
| WO | WO 99/18987 | 4/1999 |
| WO | WO 99/54485 | 10/1999 |
| WO | WO 00/20458 | 4/2000 |
| WO | WO 00/20621 | 4/2000 |

OTHER PUBLICATIONS

Li, et al, 1996, PNAS, 93: 11047–11052.*
Hollinger, et al, 1999, Cancer and Metastasis Reviews, 18: 411–419.*
Winter, et al, 1993, Immunol. Today, 14(6): 243–246.*
Iwahashi, et al, 1999, Mol. Immunol., 36: 1079–1091.*
Murdoch and Finn, 2000, Blood, 15(95): 3032–3043.*
Shaw, A., 1993, Accession No. AAA03574.*
Wautier, et al, 2001, Diabetes Metab., 27: 535–542.*
Neeper, et al, 1992, J.B.C., 267(21): 14998–15004.*
Kislinger, T. et al., N$^\epsilon$–(Carboxymethyl)Lysine Adducts of Proteins Are Ligands for Receptor for Advanced Glycation End Products That Activate Cell Signaling Pathways and Modulate Gene Expression, *J. of Biological Chemistry*, 274 (44): 31740–31749 (1999).
Schmidt, A.M. et al., Activation of Receptor for Advanced Glycation End Products: A Mechanism for Chronic Vascular Dysfunction in Diabetic Vasculopathy and Atherosclerosis, *Circ. Res.* 84:489–497 (1999).
PCT International Search Report mailed Nov. 13, 2002 for PCT/US01/17447; international filing date May 30, 2001.
Chitaley et al., "Antagonism of Rho–Kinase Stimulates Rat Penile Erection via a Nitric Oxide–Independent Pathway" *Nature Medicine* 7:119–122 (2001).
Crall et al., "The Extramural and Intramural Coronary Arteries in Juvenile Diabetes Mellitus" *Am. J. Med.* 64:221–230 (1978).
Degenhardt et al., "Chemical Modification of Proteins by Methylglyoxal" *Cell Mol. Biol.*, 44:1139–1145 (1998).
Dyer et al., "Formation of Pentosidine during Nonenzymatic Browning of Proteins by Glucose" *J. Biol. Chem.*, 266:11654–11660 (1991).
Dyer et al., "Accumulation of Maillard Reaction Products in Skin Collagen in Diabetes and Aging" *J. Clin. Invest.*, 91:2463–2469 (1993).
Hamby et al., "Reappraisal of the role of the diabetic State in Coronary Artery Disease" *Chest*, 2:251–257 (1976).
Hammes et al., "Diabetic Retinopathy Risk Correlates with Intracellular Concentrations of the Glycoxidation Product Nε–(Carboxymethyl) Lysine Independently of Glycohaemoglobin Concentrations" *Diabetologia*, 42:603–607 (1999).
Hoffman et al., "RAGE Mediates a Novel Proinflammatory Axis: A Central Cell Surface Receptor for S100/Calgranulin Polypeptides" *Cell*, 97:889–901 (1999).

(Continued)

*Primary Examiner*—Elizabeth Kemmerer
*Assistant Examiner*—Sandra Wegert
(74) *Attorney, Agent, or Firm*—Kilpatrick Stockton LLP

(57) ABSTRACT

Provided are methods to detect of modulators of the Receptor for Advanced Glycated Endproducts (RAGE). The invention comprises a method for detection of RAGE modulators comprising: adsorbing a RAGE ligand onto a solid surface; adding a compound of interest and a protein comprising RAGE or fragment thereof, to the preadsorbed ligand; adding an antibody which binds to RAGE or fragment thereof and a secondary antibody which binds to the anti-RAGE antibody; measuring the secondary antibody bound to the anti-RAGE antibody; and comparing the amount of RAGE bound to the ligand in the presence of varying amounts of the compound of interest. In an embodiment, the fragment of RAGE is sRAGE. In one aspect, the invention use of compounds detected by the method for treatment of AGE-related syndromes including complications associated with diabetes, kidney failure, lupus nephritis or inflammatory lupus nephritis, amyloidoses, Alzheimer's disease, cancer, inflammation, and erectile dysfunction.

21 Claims, 15 Drawing Sheets

OTHER PUBLICATIONS

Hori et al, "The Receptor for Advanced Glycation End Products (RAGE) Is a Cellular Binding Site for Amphoterian" *J. Biol. Chem.*, 270:25752–761 (1995).

Huttunen et al., "Receptor for Advanced Glycation End Products (RAGE)–Mediated Neurite Outgrowth and Activation of NF–κB Require the Cytoplasmic Domain of the Receptor but Different Downstream Signaling Pathways" *J Biol Chem.*, 274:19919–24 (1999).

Johnson et al., "Antioxidant with Marked Lipid– and Glucose–Lowering Activity in Diabetic Rats and Mice" *Diabetes*. 42: 1179–86, (1993).

Kannel et al, "Diabetes and Cardiovascular Disease: The Framingham Study" *J. Am. Med. Assoc.*, 241:2035–2038 (1979).

Kannel et al., "Diabetes and Glucose Tolerance as Risk Ractors for Cardiovascular Disease. The Framingham Study" *Diab. Care*, 2:120–126. (1979).

Kumar et al., "Rage at the Blood–Brain Barrier Mediated Neurovascular Dysfunction Caused by Amyloidβ$_{1-40}$ Peptide" Neurosci. Program, p141–#275.19 (2000).

Leder et al., "v–Ha–ras Transgene Abrogates the Initiation Step in Mouse Skin Tumorigenesis: Effects of Phorbol Esters and Retinoic Acid" *Proc. Natl. Acad. Sci.*, 87:9178–9182 (1990).

Li et al., "Characterization and Functional Analysis of the Promoter of RAGE, the Receptor for Advanced Glycation End Products" *J. Biol. Chem.*, 272:16498–16506 (1997).

Li et al., "Sp1–Binding Elements in the Promoter of RAGE Are Essential for Amphoterin–Mediated Gene Expression in Cultured Neuroblastoma Cells" *J. Biol. Chem.*, 273:30870–30878 (1998).

Lugering et al., "The Myeloic Related Protein MRP8/14 (27E10 Antigen)—Usefulness as a Potential Marker for Disease Activity in Ulcerative Colitis and Putative Biological Function" *Eur. J. Clin. Invest.*, 25:659–664 (1995).

Miyata et al., "β$_2$–Microglobulin Modified with Advanced Glycation End Products Is a Major Component of Hemodialysis–Associated Amyloidosis" *J. Clin. Invest.*, 92:1243–1252 (1993).

Miyata et al., "The Receptor for Advanced Glycation End Products (RAGE) Is a Central Mediator of the Interaction of AGE–β$_2$Microglobulin with Human Mononuclear Phagocytes Via an Oxidant–Sensitive Pathway" *J. Clin. Invest.*, 98:1088–1094 (1996).

Needleman and Wunsch, "A General Method Applicable to the Search for Similarities in the Amino Acid Sequence of Two Proteins" *J. Mol. Biol.* 48:443–453 (1970).

Neeper et al., "Cloning and Expression of a Cell Surface Receptor for Advanced Glycosylation End Products of Proteins" *J. Biol. Chem.*, 267:14998–15004 (1992).

Park et al., "Suppression of Accelerated Diabetic Atherosclerosis by the Soluble Receptor for Advanced Glycation Endproducts" *Nature Med.*, 4:1025–1031 (1998).

Parkkinen et al., "Amphoterin, the 30–kDa Protein in a Family of HMG1–Type Polypeptides" *J. Biol. Chem.* 268:19726–19738 (1993).

Pearson and Lipman, "Improved Tools for Biological Sequence Comparison" *Proc. Natl. Acad. Sci. (USA)*, 85:2444–2448 (1988).

Pyorala et al., "Diabetes and Atherosclerosis: an Epidemiologic View" *Diab. Metab. Rev.*, 3:463–524 (1987).

Rammes et al., "Myeloid–Related Protein (MRP) 8 and MRP14, Calcium–Binding Proteins of the S100 Family, Are Secreted by Activated Monocytes via a Novel, Tubulinp–Dependent Pathway" *J. Biol. Chem.*, 272:9496–9502 (1997).

Rauvala et al., "Isolation and Some Characteristics of an Adhesive Factor of Brain That Enhances Neurite Outgrowth in Central Neurons" *J. Biol. Chem.*, 262:16625–16635 (1987).

Reddy et al., "Nε–(Carboxymedthyl)Lysine Is a Dominant Advanced Glycation End Product (AGE) Antigen in Tissue Proteins" *Biochem.*, 34:10872–10878 (1995).

Ritthaler et al, "Expression of Receptors for Advanced Glycation End Products in Peripheral Occlusive Vascular Disease," *Amer. J. Path.*, 146:688–694 (1995).

Robertson, et al., "Atherosclerosis in Persons with Hypertension and Diabetes Mellitus" *Lab Invest.*, 18:538–551 (1968).

Schafer et al., "The S100 Family of EF–Hand Calcium–Binding Proteins: Functions and Pathology" *TIBS*, 21:134–140 (1996).

Schleicher et al., "Increased Accumulation of the Glycoxidation Product Nε–(Carboxymethyl)Lysine in Human Tissues in Diabetes and Aging" *J. Clin. Invest.*, 99(3):457–468 (1997).

Schmidt et al., "The V–Domain of Receptor for Advanced Glycation Endproducts (RAGE) Mediates Binding of AGEs: A Novel Target for Therapy of Diabetic Complications" *Circ. (Suppl.)*, vol. 96, #8 (1997).

Schmidt et al., "Isolation and Characterization of Two Binding Proteins for Advanced Glycosylation End Products from Bovine Lung Which Are Present on the Endothelial Cell Surface" *J. Biol. Chem.*, 267:14987–14997 (1992).

Schmidt et al., "The Dark Side of Glucose" *Nature Med.*, 1:1002–1004 (1995).

Smith and Waterman, "Comparison of Biosequences" *Adv. Appl. Math.* 2:482–487 (1981).

Taguchi et al., "Blockade of RAGE—Amphoterin Signalling Suppresses Tumour Growth and Metastases" *Nature*, 405:354–360 (2000).

Tanaka et al., "The Receptor for Advanced Glycation End Products Is Induced by the Glycation Products Themselves and Tumor Necrosis Factor–α through Nuclear Factor–κB, and by 17β–Estradiol through Sp–1 in Human Vascular Endothelial Cells" *J. Biol. Chem.*, 275:25781–25790 (2000).

Teillet et al., "Food Restriction Prevents Advanced Glycation End Product Accumulation and Retards Kidney Aging in Lean Rats" *J. Am. Soc. Nephrol.*, 11:1488–1497 (2000).

Vlassara et. al., "Advanced Glycation End–products and Atherosclerosis" *The Finnish Medical Society DUODECIM, Ann. Med.*, 28:419–426 (1996).

Waller et al., "Status of the Coronary Arteries at Necropsy in Diabetes Mellitus with Onset after Age 30 Years" *Am. J. Med.*, 69:498–506 (1980).

Wautier et al., "Receptor–Mediated Endothelial Cell Dysfunction in Diabetic Vasculopathy: Soluble Receptor for Advanced Glycation End Products Blocks Hyperpermeability in Diabetic Rates" *J. Clin. Invest.*, 97:238–243 (1996).

Wautier et al., "Advanced Glycation End Products (AGEs) on the Surface of Diabetic Erythrocytes Bind to the Vessel Wall via a Specific Receptor Inducing Oxidant Stress in the Vasculature: A Link between Surface–Associated AGEs and Diabetic Complications" *Proc Nat'l Acd Sci* 91:7742–7746 (1994).

Yan et al., "Enhanced Cellular Oxidant Stress by the Interaction of Advanced Glycation End Products with Their Receptors/Binding Proteins" *J. Biol. Chem.*, 269:9889–9887, (1994).

Yan et al., "Receptor–Dependent Cell Stress and Amyloid Accumulation in Systemic Amyloidosis" *Nat. Med.*, 6:643–651 (2000).

Yan et al., "RAGE and Amyloid–β Peptide Neurotoxicity in Alzheimer's Disease" *Nature*, 382:685–691 (1996).

Yan et al., "An Intracellular Protein That Binds Amyloid–β Peptide and Mediates Neurotoxicity in Alzheimer's Disease" *Nature*, 389:689–695, (1997).

Yan et al., "Amyloid–β Peptide—Receptor for Advanced Glycation Endproduct Interaction Elicits Neuronal Expression of Macrophage–Colony Stimulating Factor: A Proinflammatory Pathway in Alzheimer Disease" *Proc. Natl. Acad. Sci.*, 94:5296–5301 (1997).

Zimmer et al., "The S100 Protein Family: History, Function, and Expression" *Brain Res. Bull.*, 37:417–429 (1995).

Albanell, J. et al., Trastuzumab, a Humanized Anti–Her2 Monoclonal Antibody, for the Treatment of Breast Cancer, *Drugs Today*, 35(12):931–46 (1999).

Holliger, P. et al., Engineering Antibodies for the Clinic, *Cancer Metastasis Rev.*, 18:411–9 (1999).

Iwahashi, M. et al., CDR Substitutions of a Humanized Monoclonal Antibody (CC49): Contributions of Individual CDRs to Antigen Binding and Immunogenicity, *Mol Immunol.*, 36:1079–91 (1999).

Rapley, R., The Biotechnology and Applications of Antibody Engineering, *Mol. Biotechnol*, 3:139–54 (1995).

Winter, G. et al., Humanized Antibodies, *Immunol. Today*, 14:243–246 (1993).

Wu, T., From Esoteric Theory to Therapeutic Antibodies, *Appl. Biochem. Biotechnol.*, 47:107–17 (1994).

* cited by examiner

A.

M91211: AMINO ACID SEQUENCE OF HUMAN RAGE (SEQ ID NO: 1)

GAAGTAVGAWVLVLSLWGAVVGAQNITARIGEPLVLKCKGAPKK

PPQRLEWKLNTGRTEAWKVLSPQGGGPWDSVARVLPNGSLFLPAVGIQDEGIFRCQAM

NRNGKETKSNYRVRVYQIPGKPEIVDSASELTAGVPNKVGTCVSEGSYPAGTLSWHLD

GKPLVPNEKGVSVKEQTRRHPETGLFTLQSELMVTPARGGDPRPTFSCSFSPGLPRHR

ALRTAPIQPRVWEPVPLEEVQLVVEPEGGAVAPGGTVTLTCEVPAQPSPQIHWMKDGV

PLPLPPSPVLILPEIGPQDQGTYSCVATHSSHGPQESRAVSISIIEPGEEGPTAGSVG

GSGLGTLALALGILGGLGTAALLIGVILWQRRQRRGEERKAPENQEEEEERAELNQSE
EPEAGESSTGGP

B.

AMINO ACID SEQUENCE OF HUMAN sRAGE (SEQ ID NO:2)

GAAGTAVGAWVLVLSLWGAVVGAQNITARIGEPLVLKCKGAPKKPPQRLEWKLNTGRTEAWKV
LSPQGGGPWDSVARVLPNGSLFLPAVGIQDEGIFRCQAMNRNGKETKSNYRVRVYQIPGKPEIV
DSASELTAGVPNKVGTCVSEGSYPAGTLSWHLDGKPLVPNEKGVSVKEQTRRHPETGLFTLQS
ELMVTPARGGDPRPTFSCSFSPGLPRHRALRTAPIQPRVWEPVPLEEVQLVVEPEGGAVAPGG
TVTLTCEVPAQPSPQIHWMKDGVPLPLPPSPVLILPEIGPQDQGTYSCVATHSSHGPQESRAVSI
SIIEPGEEGPTAGSVGGSGLG

AMINO ACID SEQUENCE OF THE V-DOMAIN OF HUMAN RAGE (SEQ ID NO: 3)

AQNITARIGEPLVLKCKGAPKKPPQRLEWKLNTGRTEAWKVLSPQGGGPWDSVARVL

PNGSLFLPAVGIQDEGIFRCQAMNRNGKETKSNYRVRVYQIPGKPEIVDSASELT

D.

AMINO ACID SEQUENCE FRAGMENT OF THE V-DOMAIN OF HUMAN RAGE (SEQ ID NO: 4)

AQNITARIGEPLVLKCKGAPKKPPQRLEWK

FIG. 2
(CONT)

METHODS TO IDENTIFY COMPOUNDS THAT MODULATE RAGE

CROSS REFERENCE TO RELATED APPLICATIONS

This application claims priority to provisional patent application 60/207,342, filed May 30, 2000.

FIELD OF THE INVENTION

The present invention relates to regulation of the Receptor for Advanced Glycated Endproducts (RAGE). More particularly, the present invention describes methods for the rapid, high-throughput identification of modulators of RAGE.

BACKGROUND OF THE INVENTION

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycosylation End Products (AGEs). Factors which promote formation of AGEs included delayed protein turnover (e.g. as in amyloidoses), accumulation of macromolecules having high lysine content, and high blood glucose levels (e.g. as in diabetes) (Hori et al., *J. Biol. Chem.* 270:25752–761, (1995)). AGEs have been implicated in a variety of disorders including complications associated with diabetes and normal aging.

AGEs display specific and saturable binding to cell surface receptors on monocytes, macrophages, endothelial cells of the microvasculature, smooth muscle cells, mesengial cells, and neuroris. The Receptor for Advanced Glycated Endproducts (RAGE) is a member of the immunoglobulin super family of cell surface molecules. The extracellular (N-terminal) domain of RAGE includes three immunoglobulin-type regions: one V (variable) type domain followed by two C-type (constant) domains (Neeper et al., *J. Biol. Chem.*, 267:14998–15004 (1992); Schmidt et al., *Circ.* (Suppl.) 96#194 (1997)). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al., *J. Biol. Chem.* 270:25752–761 (1995)). Increased levels of RAGE are also found in aging tissues (Schleicher el at., *J. Clin. Invest.*, 99 (3): 457–468 (1997)), and the diabetic retina, vasculature and kidney (Schmidt et el., *Nature Med.*, 1:1002–1004 (1995)). Activation of RAGE in different tissues and organs leads to a number of pathophysiological consequences. RAGE has been implicated in a variety of conditions including: acute and chronic inflammation (Hoffman et al. Cell 97:889–901 (1999)) the development of diabetic late complications such as increased vascular permeability (Wautier et al., J. Clin. Invest., 97:238–243 1996, nephropathy (Teillet et. al., *J. Am. Soc. Nephrol.*, 11:1488–1497 (2000), atherosclerosis (Vlassara et. al., *The Finnish Medical Society DUODECIM. Ann. Med.*, 28:419–426 (1996), and retinopathy (Hammes et al. *Diabetologia*, 42:603–607 (1999)). RAGE has also been implicated in Alzheimer's disease (Yan et al., *Nature*, 382:685–691 (1996)); erectile dysfunction; and in tumor invasion and metastasis (Taguchi et al., *Nature*, 405:354–357 (2000)).

In addition to AGEs, other compounds can bind to, and modulate RAGE. In normal development, RAGE interacts with amphoterin, a polypeptide which mediates neurite outgrowth in cultural embryonic neurons (Hori et. al., 1995). RAGE has also been shown to interact with calgranulin-like ligands and β-amyloid (Yan et. al., *Nature*, 389:689–695, (1997); Yan et al., *Nature*, 382:685–691 (1996); Yan et al., *Proc. Natl. Acad. Sci.* 94:5296–5301 (1997)).

Binding of ligands such as AGEs, S100/calgranulin, β-amyloid, CML ($N^\epsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is a logical target for down-regulation of the pathophysiological changes brought about by excessive concentrations of AGEs and other ligands for RAGE.

Thus, there is a need for the methods to discover compounds which modulate binding of physiological ligands to the RAGE receptor. The method should comprise an assay which is sensitive and yet highly specific. Preferably, the method should utilize RAGE, or the binding site of RAGE itself, thereby allowing the development of modulators which vary in structure and physiological effect. Ideally, the method should lend itself to high throughput, automative techniques suitable for large scale screening of multiple compounds.

SUMMARY

The present invention relates to the use of a high throughput assay for the discovery of compound that modulate RAGE. In one aspect, the present invention comprises a method for detection of RAGE modulators comprising: (a) adsorbing a RAGE ligand onto a solid surface; (b) adding a compound of interest and a protein comprising RAGE comprising SEQ ID NO: 1 or fragment thereof to the preadsorbed ligand; (c) adding an anti-RAGE antibody which binds to the RAGE protein or fragment thereof; (d) determining the amount of RAGE protein or fragment thereof bound to the ligand by measuring the amount of anti-RAGE antibody bound to the solid surface; and (e) comparing the amount of RAGE protein or fragment thereof bound to the ligand in the presence of varying amounts of the compound of interest.

In another aspect, the present invention comprises a method for detection of RAGE modulators comprising: (a) adsorbing a RAGE ligand onto a solid surface; (b) adding a compound of interest and a protein comprising RAGE comprising SEQ ID NO: 1 or fragment thereof to the preadsorbed ligand; (c) adding an anti-RAGE antibody which binds to the RAGE protein or fragment thereof and a secondary antibody which binds to the anti-RAGE antibody; (d) measuring the secondary antibody bound to the anti-RAGE antibody; and (e) comparing the amount of RAGE bound to the ligand in the presence of varying amounts of the compound of interest.

In another aspect, the invention comprises compounds identified by the methods of the invention.

In yet another aspect, the invention comprises a kit for detection of RAGE modulators comprising: (a) a solid surface comprising a RAGE ligand; (b) a separately packaged solution comprising a protein comprising RAGE comprising SEQ ID NO: 1 or fragment thereof; (c) a detection system comprising at least one agent which specifically binds to the RAGE protein or fragment thereof; (d) separately packaged reagents for the detection system; and (e) instructions for use.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the details set forth in the following description and drawings. The invention is capable of other embodiments and of being practiced or carried out in various ways.

From the foregoing summary, it is apparent that an object of the present invention is to provide a rapid, high-throughput method for the detection of RAGE modulators. These, together with other objects of the present invention, along with the various features of novelty which characterize the invention, are pointed out with particularity in the claims annexed to and forming apart of this document

BRIEF DESCRIPTION OF THE DRAWINGS

Various features, aspects and advantages of the present invention will become more apparent with reference to the following description, appended claims, and accompanying drawings.

FIG. 1 shows a schematic representation of an embodiment of the method of the present invention.

DETAILED DESCRIPTION OF THE INVENTION

Figure 2:
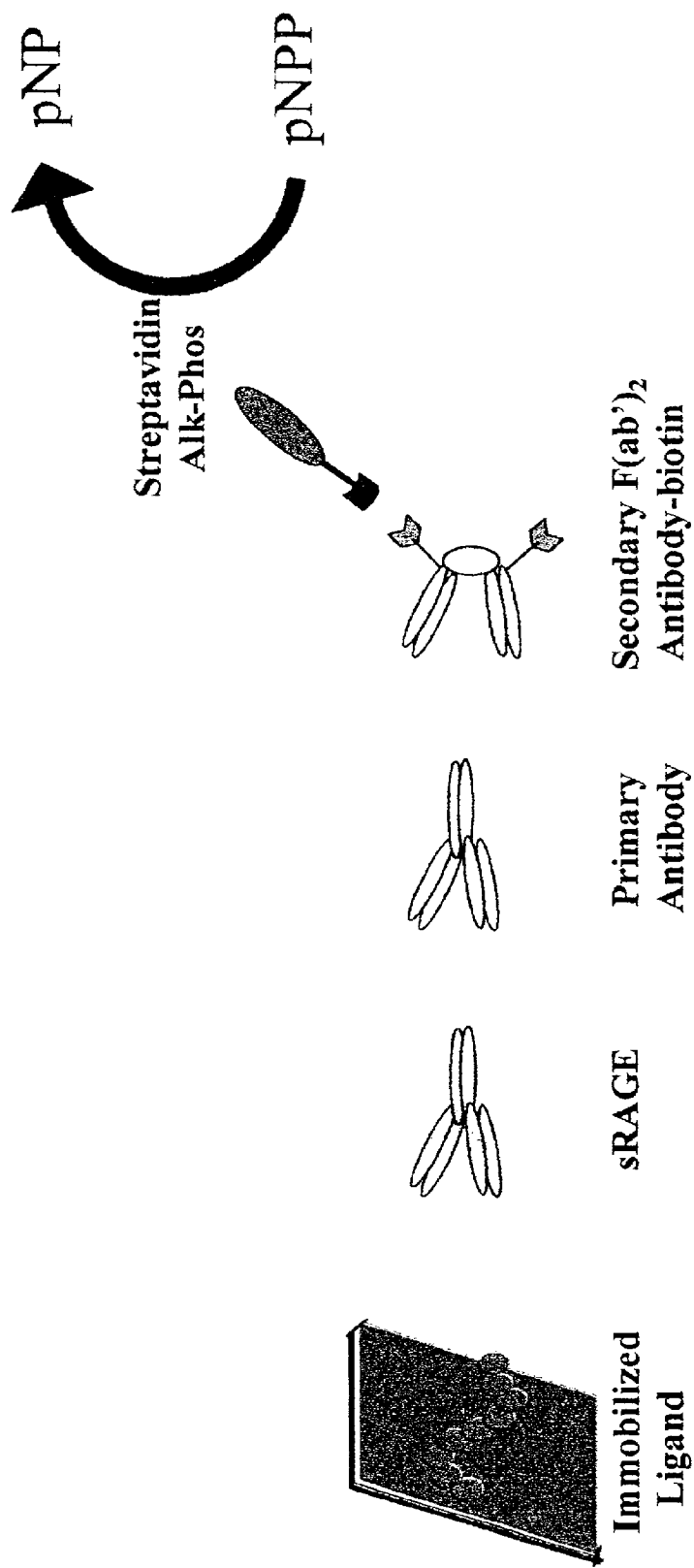
FIG. 2 shows an aspect of an embodiment of the present invention comprising: (A) SEQ ID NO: 1, the amino acid sequence for human RAGE as reported in GenBank/EMBL database, accession number XM004205; (B) SEQ ID NO: 2, the amino acid sequence of human sRAGE; (C) SEQ ID NO: 3, the amino acid sequence of the V-domain of human RAGE; and (D) SEQ ID NO: 4, the N-terminal fragment of the V-domain of human RAGE.

The present invention relates to the use of a high throughput assay for the discovery of compounds that modulate RAGE. The method measures binding of ligands to RAGE, or fragments of RAGE, under conditions in which the physiological and structural integrity of the receptor is maintained. Those compounds which bind are assessed for physiological activity.

In one aspect, the present invention comprises a method for detection of RAGE modulators comprising: (a) adsorbing a RAGE ligand onto a solid surface; (b) adding a compound of interest and a protein comprising RAGE comprising SEQ ID NO: 1 or fragment thereof to the preadsorbed ligand; (c) adding anti-RAGE antibody which binds to the RAGE protein or fragment thereof; and (d) determining the amount of RAGE protein or fragment thereof bound to the ligand by measuring the amount of anti-RAGE antibody bound to the solid surface; and (e) comparing the amount of RAGE protein or fragment thereof bound to the ligand in the presence of varying amounts of the compound of interest.

In an embodiment, the fragment of RAGE is the soluble, extracellular portion of RAGE (sRAGE), as defined by the amino acid sequence SEQ ID NO: 2, or a sequence substantially homologous thereto. In another embodiment, the fragment of RAGE is the V-domain of RAGE, as defined by the amino acid sequence SEQ ID NO: 3, or a sequence substantially homologous thereto. In yet another embodiment, the fragment of RAGE is a fragment of the V-domain of RAGE, as defined by the amino acid sequence SEQ ID NO: 4, or a sequence substantially homologous thereto. Preferably, the method comprises measuring the ability of the compound of interest to modulate the ability of RAGE, or protein substantially homologous thereto, to activate cellular processes. More preferably, agonists comprise stimulation of RAGE-activated cellular processes and antagonists comprise inhibition of RAGE-activated cellular processes. Even more preferably, the cellular process comprises activation of NF-YB gene transcription.

In an embodiment, the antibody to RAGE comprises a monoclonal antibody. In an embodiment, the antibody to RAGE comprises polyclonal antibody.

Preferably, the method further comprises addition of a second antibody which recognizes the anti-RAGE antibody. More preferably, the anti-RAGE antibody and the secondary antibody are allowed to complex prior to being added. Also preferably, the method further comprises a calorimetric assay for the secondary antibody.

In an embodiment, the solid surface comprises a reaction vessel. In another embodiment, the solid surface comprises a dip-stick.

Preferably, the ligand comprises an advanced glycated endproduct, or fragment thereof. Also preferably, the ligand comprises carboxymethyl-lycine-modified AGE. Also preferably, the ligand comprises β-amyloid. Also preferably, the ligand comprises calgranulin. Also preferably, the ligand comprises S-100b. Also preferably, the ligand comprises amphoterin.

Preferably, the compound of interest comprises a peptide. Also preferably, the compound of interest comprises a peptidomimetic. Also preferably, the compound of interest comprises an organic compound. Also preferably, the compound of interest comprises an inorganic compound. Also preferably, the compound of interest comprises a lipid. Also preferably, the compound of interest comprises a carbohydrate. Also preferably, the compound of interest comprises nucleic acid.

The invention relates to the use of a physiologically relevant binding assay to discover compounds identified which modulate RAGE. In one aspect, the invention comprises compounds identified by a method having steps comprising: (a) adsorbing a RAGE ligand onto a solid surface; (b) adding a compound of interest and a protein comprising RAGE comprising SEQ ID NO: 1 or fragment thereof to the preadsorbed ligand; (c) adding anti-RAGE antibody which binds to RAGE protein or a fragment thereof; (d) determining the amount of RAGE protein or a fragment thereof bound to the ligand by measuring the amount of anti-RAGE antibody bound to the solid surface; and (e) comparing the amount of RAGE protein or a fragment thereof bound to the ligand in the presence of varying amounts of the compound of interest.

In an embodiment, the fragment of RAGE is the soluble, extracellular portion of RAGE (sRAGE)), as defined by the amino acid sequence SEQ ID NO: 2, or a sequence substantially homologous thereto. In another embodiment, the fragment of RAGE is the V-domain of RAGE, as defined by the amino acid sequence SEQ ID NO: 3, or a sequence substantially homologous thereto. In yet another embodiment, the fragment of RAGE is a fragment of the V-domain of RAGE, as defined by the amino acid sequence SEQ ID NO: 4, or a sequence substantially homologous thereto.

Preferably, the method of identifying the compounds further comprises measuring the ability of the compound of interest to modulate the ability of RAGE comprising SEQ ID NO: 1 or a protein substantially homologous thereto, to activate cellular processes. Preferably, the compound identified by the methods of the invention is used to treat symptoms of diabetes and symptoms of diabetic late complications. Also preferably, the compound identified by the methods of the invention is used to treat amyloidoses. Also preferably, the compound identified by the methods of the invention is used to treat Alzheimer's disease. Also preferably, the compound identified by the methods of the invention is used to treat cancer. Also preferably, the compound identified by the methods of the invention is used to treat inflammation. Also preferably, the compound identified by the methods of the invention is used to treat kidney failure. Also preferably, the compound identified by the methods of the invention is used to treat systemic lupus nephritis or inflammatory lupus nephritis. Also preferably, the compound identified by the methods of the invention is used to treat erectile dysfunction.

The methods of the invention provide a flexible protocol which is adapted to a variety of reagents without reduction in reliability or precision. Thus, a variety of developing reagents or antibody preparations may be used. In one aspect, the present invention comprises a method for detection of RAGE modulators comprising: (a) adsorbing a RAGE ligand onto a solid surface; (b) adding a compound of interest and a protein comprising RAGE comprising SEQ ID NO: 1 or fragment thereof to the preadsorbed ligand; (c) adding anti-RAGE antibody which binds to the RAGE protein or a fragment thereof and a secondary antibody which binds to the anti-RAGE antibody; (d) measuring the secondary antibody bound to the anti-RAGE antibody; (e) comparing the amount of RAGE or fragment thereof bound to the ligand in the presence of varying amounts of the compound of interest.

In an embodiment, the fragment of RAGE is the soluble, extracellular portion of RAGE (sRAGE)), as defined by the amino acid sequence SEQ ID NO: 2, or a sequence substantially homologous thereto. In another embodiment, the fragment of RAGE is the V-domain of RAGE, as defined by the amino acid sequence SEQ ID NO: 3, or a sequence substantially homologous thereto. In yet another embodiment, the fragment of RAGE is a fragment of the V-domain of RAGE, as defined by the amino acid sequence SEQ ID NO: 4, or a sequence substantially homologous thereto.

Preferably, the method comprises measuring the ability of the compound of interest to modulate the ability of RAGE, or protein substantially homologous thereto, to activate cellular processes. More preferably, agonists comprise stimulation of RAGE-activated cellular processes and antagonists comprise inhibition of RAGE-activated cellular processes. Even more preferably, the cellular process comprise activation of NF-κB gene transcription.

Preferably, the method further comprises a colorimetric assay for the secondary antibody. In an embodiment, the anti-RAGE antibody and secondary antibody are allowed to complex prior to being added to the reaction vessel comprising RAGE, thus maintaining the RAGE binding domain in an non-antibody bound (i.e. unperturbed) state. In an embodiment, the solid surface comprises a reaction vessel. In an embodiment, the solid surface comprises a dip-stick.

In yet another aspect, the invention comprises a kit for detection of RAGE modulators comprising: (a) a solid surface comprising a RAGE ligand; (b) a separate packaged solution comprising a protein comprising RAGE comprising SEQ ID NO: 1 or fragment thereof; (c) a detection system comprising at least one agent which specifically binds to the RAGE, or fragment thereof; (c) separately packaged calorimetric reagents for the detection system; and (d) instructions for use. In an embodiment, the kit comprises a separately packaged antibody which binds to RAGE, or fragment thereof. In an embodiment, the fragment of RAGE is the soluble, extracellular portion of RAGE (sRAGE)), as defined by the amino acid sequence SEQ if NO: 2, or a sequence substantially homologous thereto. In an embodiment, the fragment of RAGE is the V-domain of RAGE, as defined by the amino acid sequence SEQ ID NO: 3, or a sequence substantially homologous thereto. In yet another embodiment, the fragment of RAGE is a fragment of the V-domain of RAGE, as defined by the amino acid sequence SEQ ID NO: 4, or a sequence substantially homologous thereto.

The present invention comprises a method for the detection of RAGE modulators which utilizes ligand and RAGE, or a fragments of RAGE, which have not been chemically modified. Thus, the method of the present invention is able to measure binding of ligands and the modification of such binding, with physiological specificity. The method is more reliable than assay systems which use radiolabelled binding partners, and is highly sensitive due to the use of an enzyme coupled development system. In addition, the assay employs non-toxic reagents which do not present a threat to laboratory personnel or the environment.

Thus, in one aspect, the invention comprises the use of ELISA type assay as a method for the detection of RAGE modulators. In an embodiment, and referring now to FIG. 1, a RAGE ligand, such as S-100b, is allowed to adsorb to the wells of a microtiter plate. The wells are then washed using buffered saline to remove the unbound ligand, and sites which comprise non-specific protein binding sites are blocked using blocking buffer containing bovine serum albumin (BSA) or another protein unrelated to RAGE binding. The blocking buffer is then removed, as for example by aspiration, and the wells washed several times to remove traces of blocking buffer. A solution comprising the compound of interest (i.e. a putative RAGE modulator) and RAGE comprising SEQ ID NO: 1, or fragment thereof, is added to each well. For example, in an embodiment, the RAGE fragment used is sRAGE (Taguchi et al., *Nature,* 405:354–360 (1996)). The mixture is incubated under conditions which allow physiological binding of the RAGE protein (e.g. sRAGE) to the immobilized ligand in each well.

Preferably, during the binding reaction of sRAGE to the immobilized ligand, a complex comprising: (a) anti-RAGE antibody (anti-RAGE); (b) biotinylated goat anti-mouse IgG (B-anti-IgG); and (c) streptavidin labeled alkaline phosphatase (S-AP), is allowed to form in a separate reaction vessel. After a suitable time for binding of sRAGE to the immobilized ligand, the reaction wells are washed to remove traces of unbound sRAGE and the compound of interest, and the anti-RAGE: B-anti-IgG: S-AP complex added to each well. The addition of the complex allows for immobilization of the alkaline phosphatase enzyme via interaction of the complex with sRAGE immobilized in the well (FIG. 1). By adding the immune complex separately, the sRAGE is allowed to bind to the ligand and compound of interest (i.e.

putative modulator) without interference due to antibody binding. The amount of alkaline phosphatase, and thus the amount of immobilized sRAGE, can then be detected using a calorimetric assay for conversion of para-nitrophenyl phosphate (pNPP) to para-nitrophenol (pNP).

As used herein, RAGE encompasses a peptide which has the fall amino acid sequence of RAGE as shown in FIG. 2A (SEQ ID NO: 1) or a portion of that amino acid sequence (Neeper et al., (1992)). The binding domain of RAGE comprises that region of the protein which is able to bind ligands with physiological specificity. A fragment of RAGE is at least 5 amino acids in length, but more preferably greater than 30 amino acids in length, but is substantially less than the full amino acid sequence. Thus, in another embodiment, the fragment of RAGE comprises sRAGE (SEQ ID NO: 2; FIG. 2B), wherein sRAGE is the RAGE protein free from the cell membrane (ark et al., *Nature Med.,* 4:1025–1031 (1998)). In another embodiment, the RAGE or fragment thereof comprises the V domain (SEQ ID NO: 3; FIG. 2C) (Neeper et al., (1992); Schmidt et al., (1997)), or a fragment thereof (SEQ ID NO: 4, FIG. 2D). In yet another embodiment, the RAGE or fragment thereof is a synthetic peptide.

The terms "substantially homologous" when referring to polypeptides refer to at least two amino acid sequences which when optimally aligned, are at least 75% homologous, preferably at least about 85% homologous, more preferably at least about 90% homologous, and still more preferably 95% homologous. Optimal alignment of sequences for aligning a comparison may be conducted using the algorithms standard in the art (e.g. Smith and Waterman, *Adv. Appl. Math.* 2:482 (1981); Needleman and Wunsch, *J. Mol. Biol.* 48:443 (1970); Pearson and Lipman, *Proc. Natl. Acad. Sci.* (USA), 85:2444 (1988)) or by computerized versions of these algorithms (Wisconsin Genetics Software Package Release 7.0, Genetics Computer Group, 575 Science Drive, Madison, Wis.).

Preferably, the concentration of ligand used for coating the solid surface (i.e. reaction wells) allows any antagonism of binding of the immobilized ligand to sRAGE to be detected. For example, referring now to FIG. 3, where sRAGE comprises 0.1 $\mu$g/ml, and anti-sRAGE antibody comprises 3.0 $\mu$g/ml, almost maximum signal is seen with 500 ng S-100b, and ligand concentrations between 10 to 500 ng/well comprise a linear increase in sRAGE binding.

Figure 4:
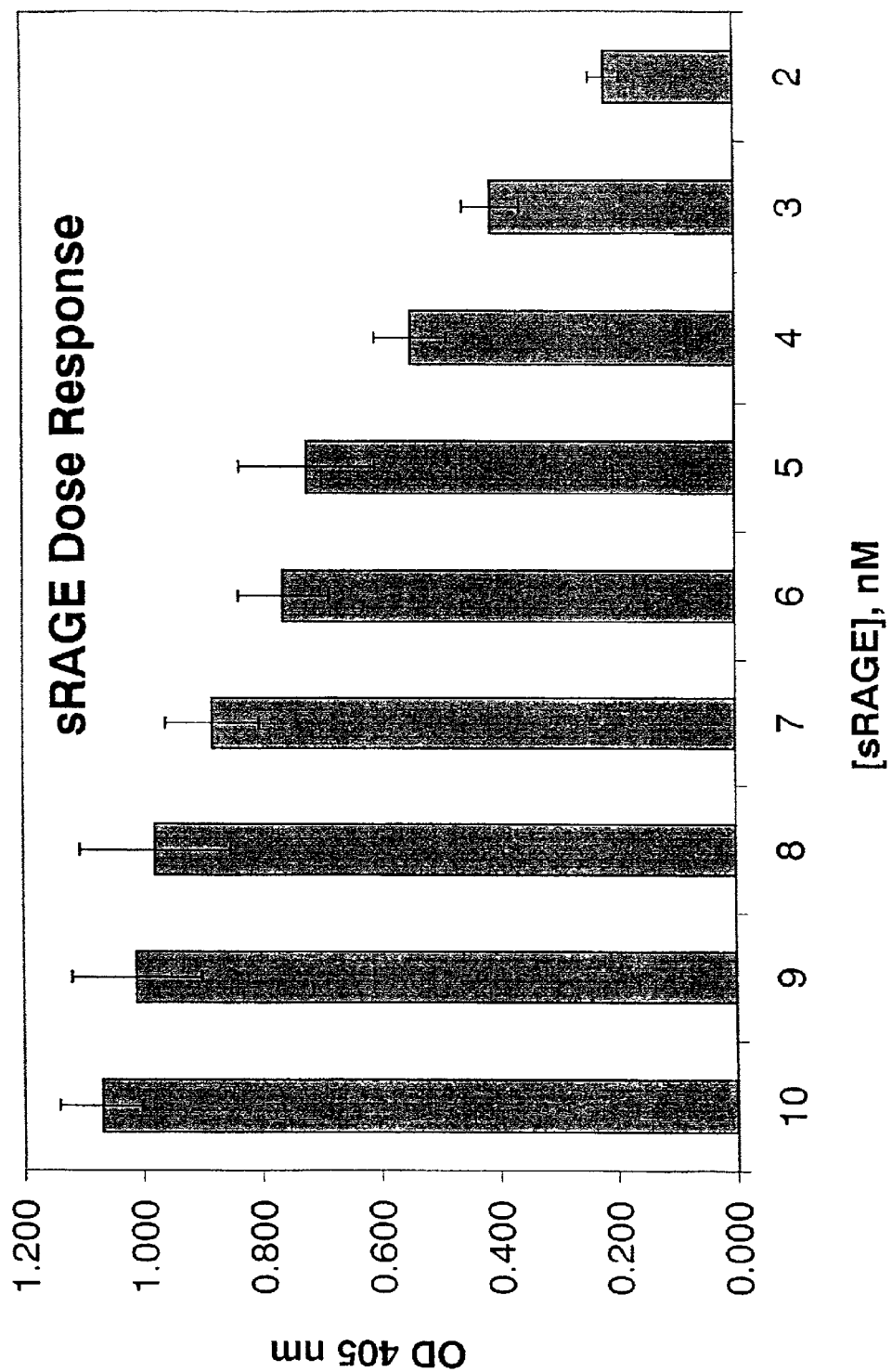
FIG. 4 shows an aspect of an embodiment of the present invention comprising optimization of sRAGE concentration where 500 ng/well S-100b was used to coat wells, and polyclonal antibody to sRAGE was present at $3.0 \times 10^{-3}$ mg/ml, and sRAGE concentration ranged from about 2 to 10 nM.

Also preferably, and referring now to FIG. 4, the assay is designed to allow selection of an amount of sRAGE which comprises a linear region of binding of sRAGE and the immobilized ligand. For example, if too low of a concentration of sRAGE is employed, the detection of binding will be difficult due to low signal. If excess sRAGE is used, however, the ability of compound of interest to compete with the immobilized ligand will be lessened due to the excess sRAGE binding to both the ligand and the compound being tested.

Also preferably, the assay is designed to allow optimization of the anti-RAGE antibody. Thus, in an embodiment, and referring now to FIG. 5, the amount of antibody used can be titered to allow for maximal signal, but not so high as to comprise high levels of background binding. More preferably, the amount of antibody allowing for maximum signal comprises a similar range of antibody regardless of the concentration of immobilized ligand.

Also preferably, the assay is optimized to be independent of solvents required for dissolving the compounds being tested. In an embodiment, and referring to FIG. 6, for dimethyl sulfoxide (DMSO) concentrations of 2%, which is the concentration of DMSO generally employed for dissolution of organic compounds of interest in the assay, the assay provides maximal signal. Even at concentrations as high as 10% DMSO, the assay provides almost maximal signal.

Figure 7:
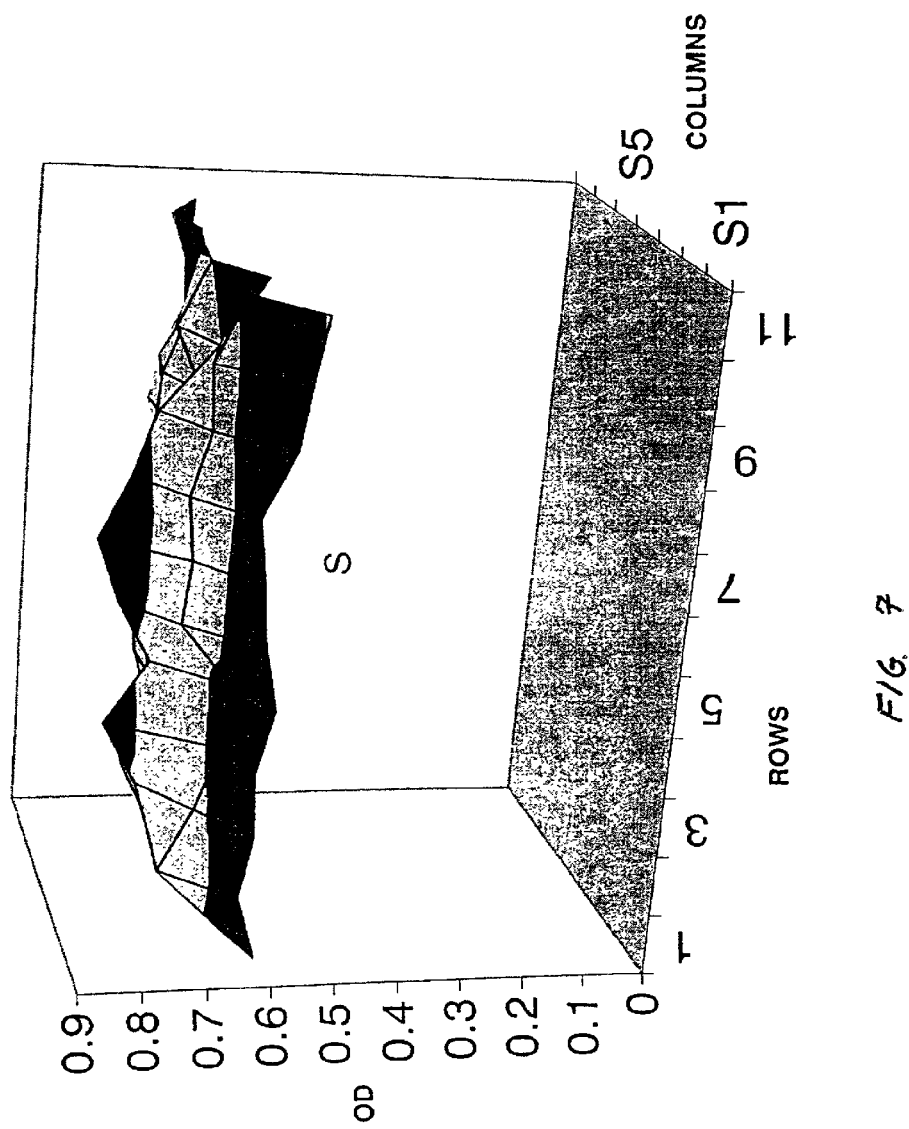
FIG. 7 shows an aspect of an embodiment of the present invention comprising the variation in sample OD for 88 samples as a function of individual well position, where the average OD comprised 0.705, the standard deviation (SD) is 0.054, and the 95% confidence value (CV) is 7.73%.

Thus, the assay allows for optimization of each component, such that variation of assay results due to environmental factors and experimental variation is minimized. Preferably, once optimized for a specific ligand, sRAGE concentration, and anti-sRAGE antibody concentration, the assay will provide a reliable assessment of sample binding affinity regardless of the specific competing compound (i.e. putative modulator) which is being tested. Also preferably, the assay comprises a high throughput assay that is reproducible and precise. Referring now to FIG. 7, in an embodiment the assay comprises a variance of less than 10%.

Without being bound to any particular theory, a premise of the assay is that binding of sRAGE to the ligand immobilized in the assay well will reflect the nature of the binding of RAGE to the ligand in vivo. Thus, in an embodiment, the immobilized ligand will bind RAGE comprising SEQ ID NO: 1, or fragment thereof, in a specific and saturable manner. For example, and referring now to FIGS. 8–11, sRAGE at concentrations ranging from about 0.3 to 480 nM binds in a saturable manner to S-000b ligand immobilized in a microtiter well. In addition, an analysis of the data by means of Scatchard transformation shows both high and low affinity sites with dissociation constants (Kd) similar to the Kd for RAGE reported previously (Hofmann et al., *Cell*, 97:889–901 (1999); Hori et al., *J. Biol. Chem.*, 270:25752–25761 (1995)).

Figure 8:
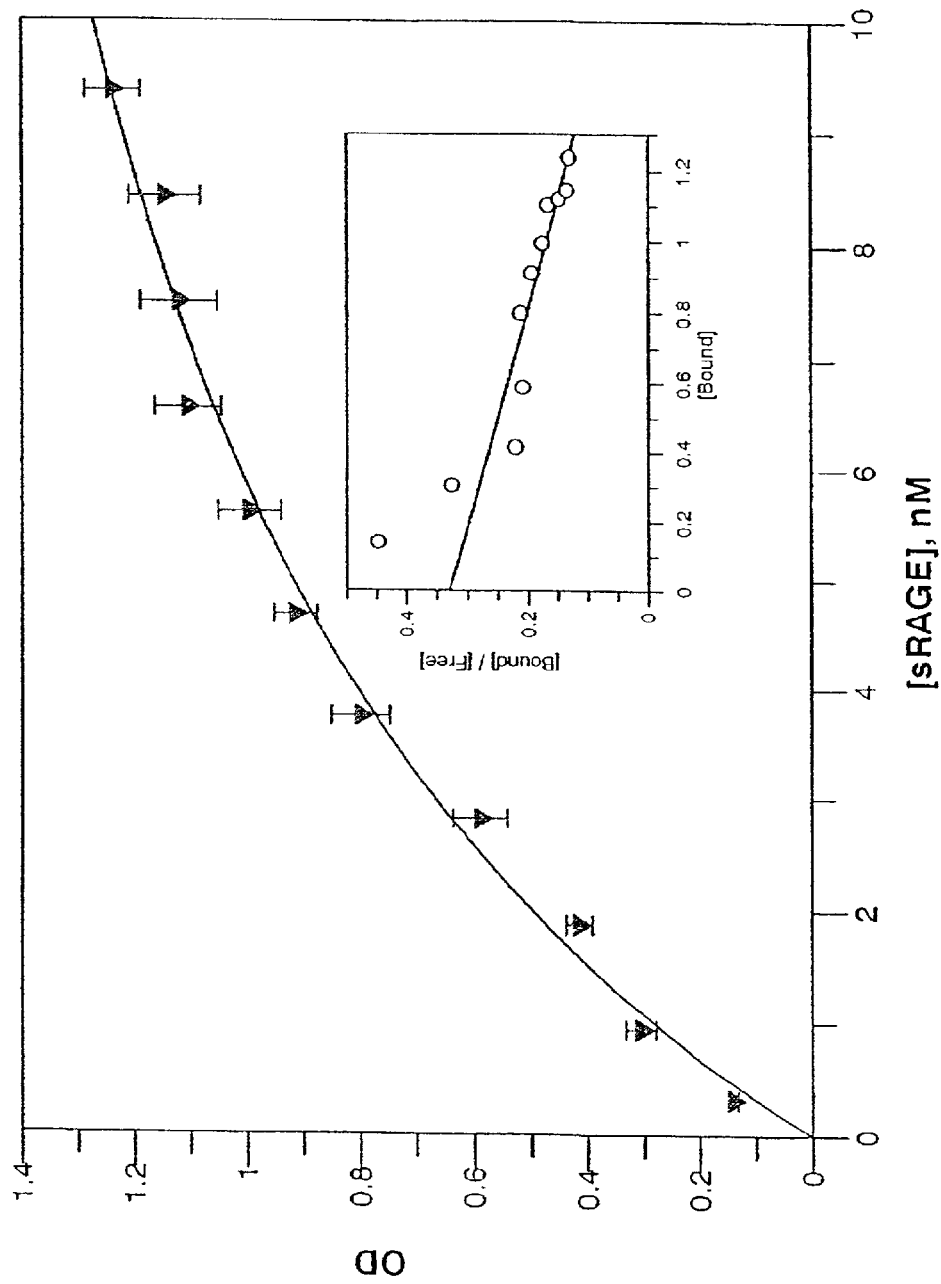
FIG. 8 shows an aspect of an embodiment of the present invention comprising a saturation curve for sRAGE binding to S-100b, where 50 ng/well S-100b was used to coat the wells, polyclonal antibody to sRAGE was present at $3.0 \times 10^{-3}$ mg/ml, and sRAGE concentration ranged from about 0.5 to 9 nM.
Figure 9:
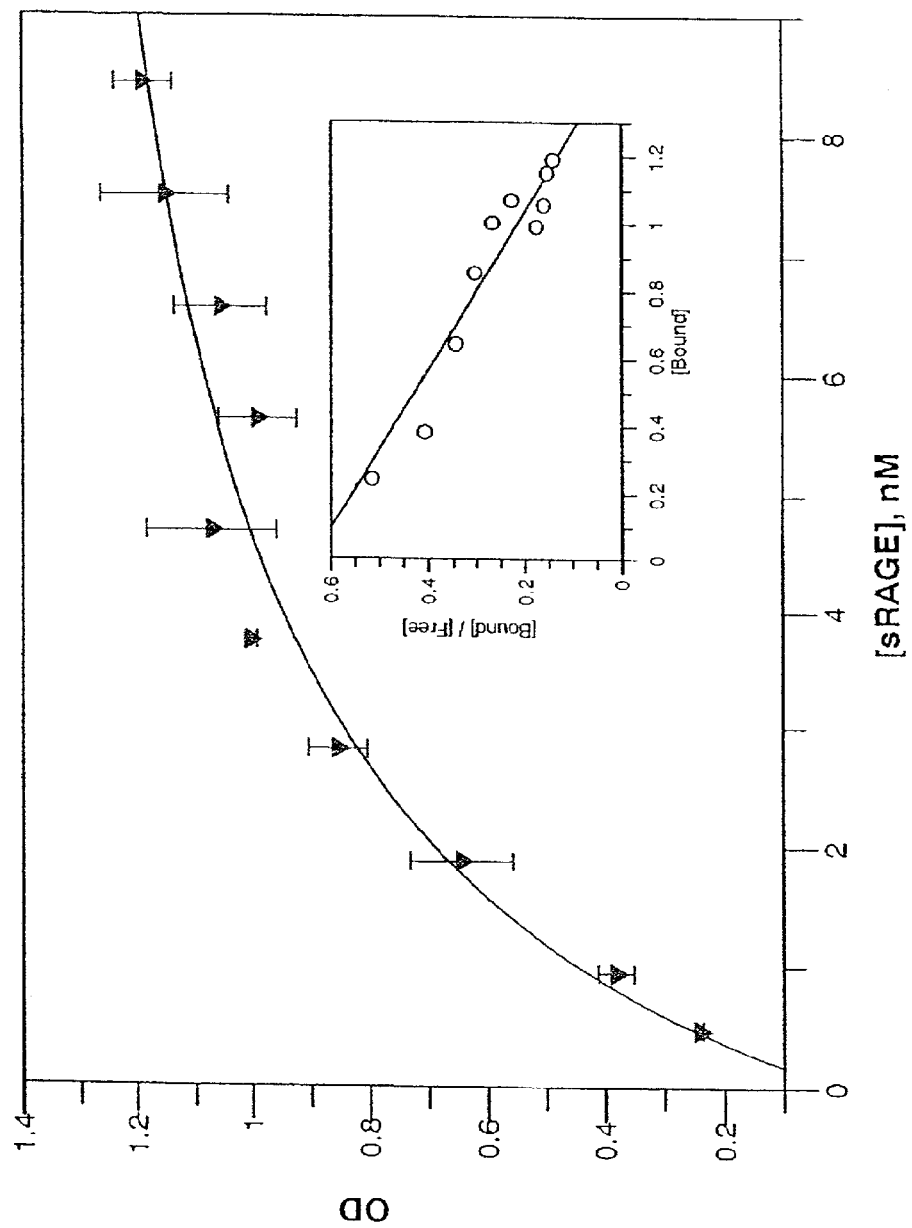
FIG. 9 shows an aspect of an embodiment of the present invention comprising a saturation curve for sRAGE binding to S-100b, where 100 ng/well S-100b was used to coat the wells, polyclonal antibody to sRAGE was present at $3.0 \times 10^{-3}$ mg/ml, and sRAGE concentration ranged from about 0.3 to 10 nM.

Preferably, the assay of the present invention is able to detect compounds that antagonize both low and high affinity binding sites. Referring now to FIGS. 8 and 9, using sRAGE at concentrations ranging from 0.3 to 10 nM, a high affinity binding site comprising a Kd of about 2–6 nM is detected. Also, referring now to FIGS. 10 and 11, using sRAGE at concentrations ranging from 24 to 480 nM, and 5 to 80 nM respectively, a lower affinity binding site comprising a Kd of about 60 nM is detected.

In an embodiment, the anti-RAGE antibody is polyclonal. Polyclonal antibodies are a heterogeneous population of antibody molecules derived from the sera of animals immunized with the antigen of interest. Adjuvants such as Freund's (complete and incomplete), peptides, oil emulsions, lysolecithin, polyols, polyanions and the like may be used to increase the immune response. Thus, in an embodiment, polyclonal antibody ato sRAGE is prepared by injection of sRAGE supplemented with an adjuvant into rabbits using methods known in the art (e.g. Schmidt et al., *J. Biol. Chem.*, 267:14987–14997 (1992)).

Monoclonal antibodies are homogeneous populations of antibodies to a particular antigen, and are generally obtained by any technique which provides for production of antibody by continuous cell lines in culture (see e.g. U.S. Pat. No. 4,873,313). For example, in an embodiment sRAGE protein is used for production of monoclonal antibodies using methods known in the art (Zymed Laboratories, San Francisco, Calif.).

Again without being bound to any particular theory, a premise of the assay is that one of the components in the detection system labeled. It is contemplated that the detection system may use reagents which are can be seen visually, and which are thereby defined as "calorimetric.: For example, in an embodiment, a complex of anti-RAGE antibody: biotinylated goat anti-human IgG: streptavidin labeled alkaline phosphatase is used to detect sRAGE bound to the ligand. The alkaline phosphatase enzyme catalyses the conversion of light yellow para-nitrophenyl phosphate (pNPP) to the pink product para-nitrophenol. It is, however, within the scope of the present invention to use variations of the detection system which are known to those in the art. For example, in a embodiment, the secondary antibody which binds to anti-RAGE antibody is labeled with streptavidin and then detected with biotinylated alkaline phosphatase. Other labeling moieties include fluorescein, digoxigenin, 2,2'-Azino-di-[3-ethylbenzthiazoline sulfonate (6)] diammonium salt, and the like. In another embodiment, streptavidin-labeled horseradish peroxidase is employed as the detection system. Alternatively, in another embodiment, a third antibody comprising biotinylated anti-goat IgG, can be used to detect a non-biotinylated anti-mouse IgG. In yet another embodiment, the anti-RAGE antibody itself may be biotinylated, and detected using streptavidin-labeled alkaline phosphatase.

The assay may be carried out with the ligand immobilized to the surface of a reaction vessel or other solid surface. For example, in an embodiment, the ligand is immobilized in a microtiter well. In another embodiment, the ligand is immobilized on a dip-stick. In this format, the assay may be performed by transferring the dipstick comprising an immobilized ligand first to solution comprising sRAGE and a test compound (or biological sample), and then to a reagent for detecting sRAGE binding to the dipstick (e.g. an anti-sRAGE antibody:biotinylated IgG: streptavidin-alkaline phosphatase complex). A reduction in signal on the dipstick as compared to a known control would indicate the sample comprises a compound which can bind to RAGE. In an embodiment, the assay can detect increased RAGE ligands in a biological sample. Preferably, such ligands include AGEs, amphoterin, (Hori et al., 1995), and β-amyloid (Yan et al., *Nature* 389:689–695, (1997); Yan et al., *Nature* 382:685–691 (1996); Yan et al., *Proc. Natl. Acad. Sci.*, 94:5296–5301 (1997)). In another embodiment, the ligand is immobilized on beads, a nylon membrane, or any other solid support.

The methods of the invention provide binding assays to identify compounds that interact with RAGE under physiological binding conditions. In this respect, physiological binding conditions comprise those conditions which result in binding affinities similar to those seen in vivo. Thus, in another aspect, the present invention comprises the compounds identified by the methods of the invention. Compounds identified by the methods of the invention may comprise several different chemical types. For example, in an embodiment the compound is a peptide. In another embodiment, the compound is a peptidomimetic. In another embodiment, the compound is an organic molecule. In another embodiment, the compound is an inorganic molecule. In some cases, the compound of interest may be derivatized to increase half-life.

The compounds of the present invention may be a peptidomimetic which is at least partly unnatural. Preferably the compound of interest may be modified to increase stability, efficacy, potency and bioavailability. The compound may be synthetically prepared. The compound may include L-, D-, or unnatural amino acids, alpha-disubstituted amino acids, N-alkyl amino acids, or lactic acid. In an embodiment, the compound comprises a peptidomimetic having a peptide backbone or amino acid replaced with a suitable mimetic.

Figure 12:
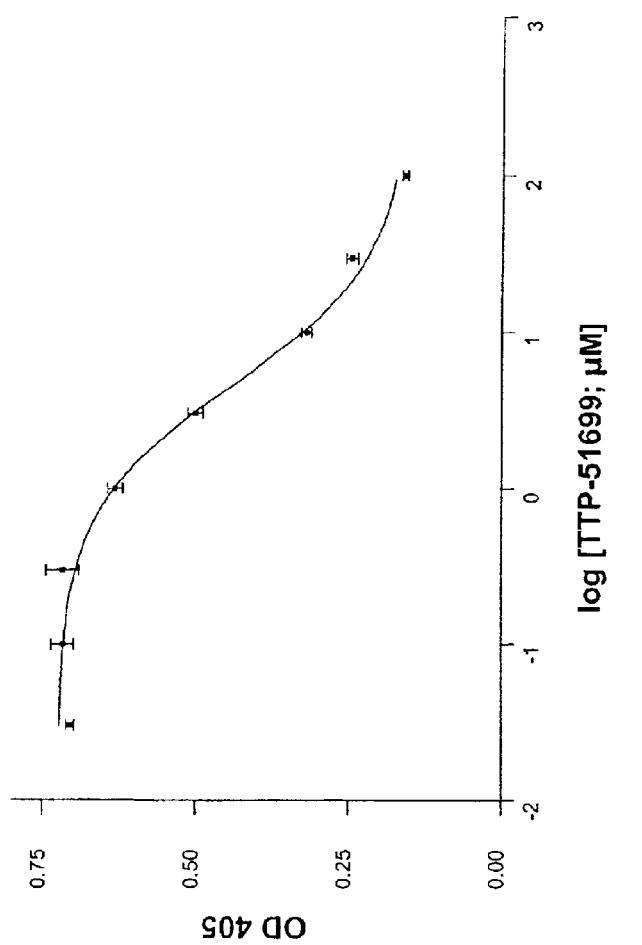
FIG. 12 shows an aspect of an embodiment of the present invention comprising inhibition of sRAGE binding by Compound 1.
Figure 13:
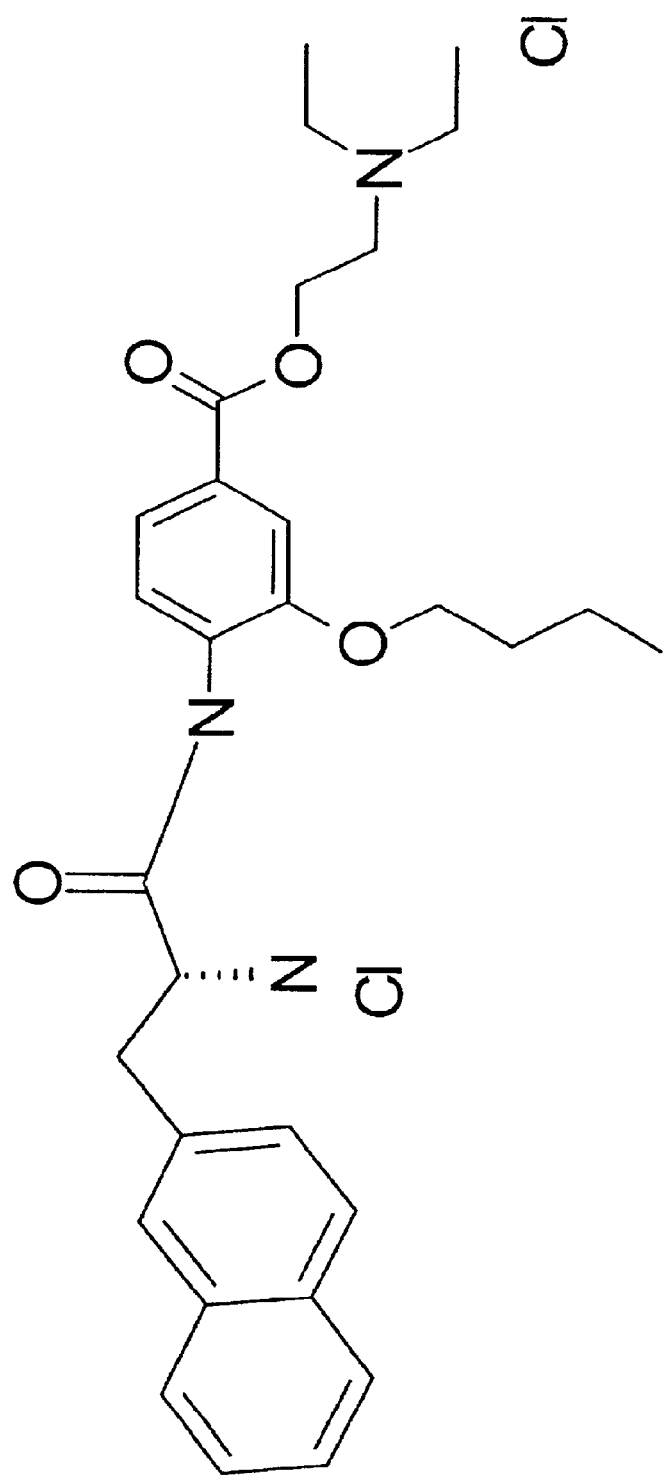
FIG. 13 shows an aspect of an embodiment of the present invention comprising the structure of Compound 1.

For example, as shown in FIG. 12, Compound 1, the structure of which is shown in FIG. 13, inhibits sRAGE binding to S-100b with $IC_{50}=1.8\pm0.2$ μM, wherein $IC_{50}$ is defined as the concentration of the agent (i.e. Compound 1) which comprises 50% inhibition of sRAGE binding.

In an embodiment, compounds identified by the binding assay are further tested as having the ability to modulate a biological activity of RAGE comprising SEQ ID NO: 1, or fragment thereof. For example, compounds can be tested for their ability to modulate RAGE induced increases in gene expression. Thus, in an embodiment and referring now to FIG. 14, compounds identified by the binding assay are used to modulate RAGE activation of NF-κB mediated transcription of a reporter gene. Preferably, compounds which modulate ligand binding to RAGE comprising SEQ ID NO: 1, or fragment thereof, will be identified as modulating the effects of RAGE on other cellular processes.

In an embodiment, the invention comprises treatment of human disease by compounds identified by the methods of the invention. Preferably, compounds identified by the methods of the invention are used to treat diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer et al., *J. Clin. Invest.,* 91:2463–2469 (1993); Reddy et al., *Biochem.,* 34:10872–10878 (1995); Dyer et al., *J. Biol. Chem.,* 266:11654–11660 (1991); Degenhardt et al., *Cell Mol. Biol.,* 44:1139–1145 (1998)). Accumulation of AGEs in the vasculature can occur focally, as in the joint amyloid composed of AGE-$\beta_2$-microglobulin found in patients with dialysis-related amyloidosis (Miyata et al., *J. Clin. Invest.,* 92:1243–1252 (1993); Miyata et al., *J. Clin. Invest.,* 98:1088–1094 (1996)), or generally, as exemplified by the vasculature and tissues of patients with diabetes (Schmidt et al., *Nature Med.,* 1:1002–1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li et al., *J. Biol. Chem.,* 272:16498–16506 (1997); Li et al., *J. Biol. Chem.,* 273:30870–30878 (1998); Tanaka et al., *J. Biol. Chem.,* 275:25781–25790(2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

Also preferably, compounds identified by the methods of the invention are used to treat atherosclerosis. Thus, it has been shown that ischemic heart disease is particularly high in patients with diabetes (Robertson, et al., *Lab Invest,* 18:538–551 (1968); Kannel et al., *J. Am. Med. Assoc.,* 241:2035–2038 (1979); Kannel et al., *Diab. Care,* 2:120–126 (1979)). In addition, studies have shown that atherosclerosis in patients with diabetes is more accelerated and extensive than in patients not suffering from diabetes (see e.g. Waller et at., *Am. J Med.* 69:498–506 (1980); Crall et. al., *Am. J. Med.* 64:221–230 (1978); Hamby et. al., *Chest.* 2:251–257 (1976); and Pyorala et al., *Diaib. Metab. Rev.,* 3:463–524 (1987)). Although the reasons for accelerated atherosclerosis in the setting of diabetes are many, it his been shown that reduction of AGEs can reduce plaque formation.

Also preferably, compounds identified by the methods of the invention are used to treat amyloidoses and Alzheimer's disease. It has been shown that RAGE binds β-sheet fibrillar material regardless of the composition of the subunits (amyloid-β peptide, amylin, serum amyloid A, prion-derived peptide) (Yan et al., *Nature,* 382:685–691 (1996); Yan et al., *Nat. Med.,* 6:643–651 (2000)). In addition, deposition of amyloid has been shown to result in enhanced expression of RAGE. For example, in the brains of patients with Alzheimer's disease (AD), RAGE expression increases in neurons and glia (Yan, et al., *Nature* 382:685–691 (1996)). The consequences of β-amyloid peptide (Aβ) interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ is shown by the inhibition of Aβ-induced cerebral vasoconstriction and transfer of the peptide across the blood-brain barrier to brain parenchyma when the receptor was blocked (Kumar et al., *Neurosci. Program,* p141-#275.19 (2000)). Inhibition of RAGE-amyloid interaction has been shown to decrease expression of cellular RAGE and cell stress markers (as well as NF-κB activation), and diminish amyloid deposition (Yan et al., *Nat. Med.,* 6:643651 (2000)) suggesting a role for RAGE-amyloid interaction in both perturbation of cellular properties in an environment enriched for amyloid (even at early stages) as well as in amyloid accumulation.

Also preferably, compounds identified by the methods of the invention are used to treat cancer. For example, amphoterin is a high mobility group I nonhistone chromosomal DNA binding protein (Rauvala et al., *J. Biol. Chem.,* 262:16625–16635 (1987); Parkikinen et al., *J. Biol. Chem.,* 268:19726–19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi et al., *Nature* 405:354–360 (2000)), and spontaneously arising papillomas in mice expressing the v-Ha-ras transgene (Leder et al., *Proc. Natl. Acad. Sci.,* 87:9178–9182 (1990)).

Also preferably, compounds identified by the methods of the invention are used to treat inflammation. Also preferably, the compounds identified by the methods of the invention are used to treat kidney failure. Also preferably, the compounds identified by the methods of the invention are used to treat systemic lupus nephritis or inflammatory lupus nephritis. For example, the S100/calgranulins have been shown to comprise a family of closely related calcium-binding polypeptides characterized by two EF-hand regions linked by a connecting peptide (Schafer et al., *TIBS,* 21:134–140 (1996); Zimmer et al., *Brain Res. Bull.,* 37:417–429 (1995); Rammes et al., *J. Biol. Chem.,* 272:9496–9502 (1997); Lugering et al., *Eur. J. Clin. Invest.,* 25:659–664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S-100/calgranulins) has a proximal role in the inflammatory cascade.

Also preferably, compounds identified by the methods of the invention are used to treat erectile dysfunction. Relaxation of the smooth muscle cells in the cavernosal arterioles and sinuses results in increased blood flow into the penis, raising corpus cavernosum pressure to culminate in penile erection. Nitric oxide is considered the principle stimulator of cavernosal smooth muscle relaxation (Chitaley et al, *Nature Medicine*, Jan.; 7(1): 119–122 (2001)). RAGE activation produces oxidants (Yan et (al., *J. Biol. Chem.*, 269:9889–9897, 1994) via an NADH oxidase-like enzyme, therefore suppressing the circulation of nitric oxide. Potentially by inhibiting the activation of RAGE signaling pathways by decreasing the intracellular production of AGEs, generation of oxidants will be attenuated. Rage blockers may promote and facilitate penile erection by blocking the access of ligands to RAGE. The calcium-sensitizing Rho-kinase pathway may play a synergistic role in cavernosal vasoconstriction to maintain penile flaccidity. The antagonism of Rho-kinase results in increased corpus cavernosum pressure, initiating the erectile response independently of nitric oxide (Wingard et. al. 2001). One of the signaling mechanisms activated by RAGE involves the Rho-kinase family such as cdc42 and rac (Huttunen et. al.,*J Biol Chem.*, 274:19919–24 (1999)). Thus, inhibiting activity ation of Rho-kinases via suppression of RAGE signaling pathways will enhance and stimulate penile erection independently of nitric oxide.

In one aspect, the present invention also provides a method for inhibiting the interaction of an AGE with RAGE in a subject which comprises administering to the subject a therapeutically effective amount of a compound identified by the methods of the invention. A therapeutically effective amount is an amount which is capable of preventing interaction of AGE/RAGE in a subject. Accordingly, the amount will vary with the subject being treated. Administration of the compound may be hourly, daily, weekly, monthly, yearly or a single event. Preferably, the effective amount of the compound comprises from about 1 ng/kg body weight to about 100 mg/kg body weight. More preferably, the effective amount of the compound comprises from about 1 $\mu$g/kg body weight to about 50 mg/kg body weight. Even more preferably, the effective amount of the compound comprises from about 10 $\mu$g/kg body weight to about 10 mg/kg body weight. The actual effective amount will be established by dose/response assays using methods standard in the art (Johnson et al., *Diabetes*. 42:1179, (1993)). Thus, as is known to those in the art, the effective amount will depend on bioavailability, bioactivity, and biodegradability of the compound.

In an embodiment, the subject is an animal. In an embodiment, the subject is a human. In an embodiment, the subject is suffering from an AGE-related disease such as diabetes, amyloidoses, renal failure, aging, or inflammation. In another embodiment, the subject comprises an individual with Alzheimer's disease. In an alternative embodiment, the subject comprises an individual with cancer. In yet another embodiment, the subject comprises an individual with systemic lupus erythmetosis, or inflammatory lupus nephritis.

In an embodiment, administration of the compound comprises intralesional, intraperitoneal, intramuscular, or intravenous injection. In an embodiment, administration of the compound comprises infusion or liposome-mediated delivery. In an embodiment, administration of the compound comprises topical application to the skin, nasal cavity, oral membranes or ocular tissue.

The pharmaceutically acceptable carriers of the invention comprise any of the standard pharmaceutically accepted carriers known in the art. In an embodiment, the carrier comprises a diluent. In an embodiment, the carrier comprises a liposome, a microcapsule, a polymer encapsulated cell, or a virus. For example, in one embodiment, the pharmaceutical carrier may be a liquid and the pharmaceutical composition in the form of a solution. In another embodiment, the pharmaceutically acceptable carrier is a solid and the composition is in the form of a powder or tablet. In a further embodiment, the pharmaceutical carrier is a gel or ointment and the composition is in the form of a suppository, cream, or liquid. Thus, the term pharmaceutically acceptable carrier encompasses, but is not limited to, any of the standard pharmaceutically accepted carriers, such as phosphate buffered saline solution, water, emulsions such as oil/water emulsions or trigyceride emulsion, various types of wetting agents, tablets, coated tablets and capsules.

For example, tablets or capsules may utilize pharmaceutically acceptable binding agents (e.g. polyvinylpyrrolidone, hydroxypropyl methylcellulose, starch); fillers (e.g. lactose, microcrystalline cellulose, calcium hydrogen phosphate); lubricants (e.g. magnesium stearate, silica or talc). Liquid preparations for oral administration may comprise syrups or suspensions prepared by conventional means with pharmaceutically acceptable additives such as suspending agents (e.g. hydrogenated fats, sorbitol syrup), emulsifying agents (e.g. lecithin), and preservatives. Preparations may contain buffer, salts, and flavoring agents as appropriate. Suitable examples of liquid carriers include water, alcohols, and oils containing additives as described above.

When administered, compounds are often rapidly cleared from the circulation. Thus, in an embodiment, compounds are modified by the covalent attachment of water-soluble polymers such as polyethylene glycol (PEG), copolymers of PEG and polypropylene glycol, polyvinylpyrrolidone or polyproline, carboxymethyl cellulose, dextran, polyvinyl alcohol, and the like. Such modifications also may increase the compound's solubility in aqueous solution, and reduce immunogenicity of the compound. Polymers such as PEG may be covalently attached to one or more reactive amino residues, sulfydryl residues or carboxyl residues. Numerous activated forms of PEG have been described, including active esters of carboxylic acid or carbonate derivatives, particularly those in which the leaving groups are N-hydroxsuccinimide, p-nitrophenol imdazole or 1-hydroxy-2-nitrobenzene-3 sulfone for reaction with amino groups, maleimido or haloacetyl derivatives for reaction with sulfydryl groups, and amino hydrazine or hydrazide derivatives for reaction with carbohydrate groups.

EXAMPLES

Features and advantages of the inventive concept covered by the present invention are further illustrated in the examples which follow.

Example 1

ELISA Assay Protocol

Generally, the protocol for detection of RAGE modulators is as follows. RAGE ligand (e.g. S-100b, $\beta$-amyloid, CML) is diluted to 5 $\mu$g/ml in buffer A (fixing buffer) (100 mM $Na_2CO_3$/$NaHCO_3$, pH 9.8) and 100 $\mu$l added to microtiter plate wells and allowed to incubate overnight at 4° C. to allow the ligand to become fixed to the surface of the wells.

Wells are then washed 3 times with 400 μl/well buffer C (wash buffer) (20 mM Imidazole, 150 mM NaCl, pH 7.2), with a 5 second soak in buffer C between each wash. Buffer B (blocking buffer) (50 mM Imidazole pH 7.2, 5% BSA, 5 mM $CaCl_2$, 5 mM $MgCl_2$) is then added to the wells and allowed to incubate for 2 hours at 37° C. to block nonspecific protein binding sites. The blocking buffer is then aspirated from the wells, and the plate washed 3 times (400 μl/well) with buffer C, with a 5 second soak in buffer C between each wash. The compound of interest, 25 μl dissolved in 2% DMSO FAC (Final Assay Concentration) and sRAGE (75 μl) ($2.2 \times 10^{-4}$ mg/ml FAC) are then added to each well, and incubated 1 hour at 37° C. Meanwhile, polyclonal antibody or monoclonal antibody for sRAGE (e.g. $3.0 \times 10^{-3}$ mg/ml and $1.9 \times 10^{-4}$ mg/ml FAC, respectively), biotinylated goat F $(ab')_2$ anti-mouse IgG (e.g. $8.0 \times 10^{-4}$ mg/ml FAC) (Biosource International, Camarillo, Calif. (TAGO)), and alkaline phosphatase labeled streptavidin ($3.0 \times 10^{-3}$ mg/ml FAC) (ZYMED, San Francisco, Calif.) are added to 5 ml of buffer D (complex buffer) (50 mM Imidazole, pH 7.2; 0.2% BSA, 5 mM $CaCl_2$, 5 mM $MgCl_2$) in a 15 ml conical tube and allowed to incubate 30 minutes at room temperature.

The solution containing sRAGE and the compound of interest is then aspirated from each well, and after 3 washes with wash buffer, with a 5 second soak between each wash, the anti-sRAGE:IgG:streptavidin-alkaline phosphatase complex is added to each well (100 μl complex per well). After 1 hour at room temperature, the solution in each well is aspirated, and the wells washed 3 times, with 5 second soaks between each wash.

The alkaline phosphatase substrate, para-nitrophenyl phosphate (pNPP) (1 mg/ml in 1 M diethanolamine, pH 9.8), is added and the color allowed to develop for 1 hr in the dark. After the addition of 10 μl stop solution per well (0.5 N NaOH; 50% methanol), the $OD_{405}$ is measured.

Example 2

Optimization of Assay Conditions

Figure 3:
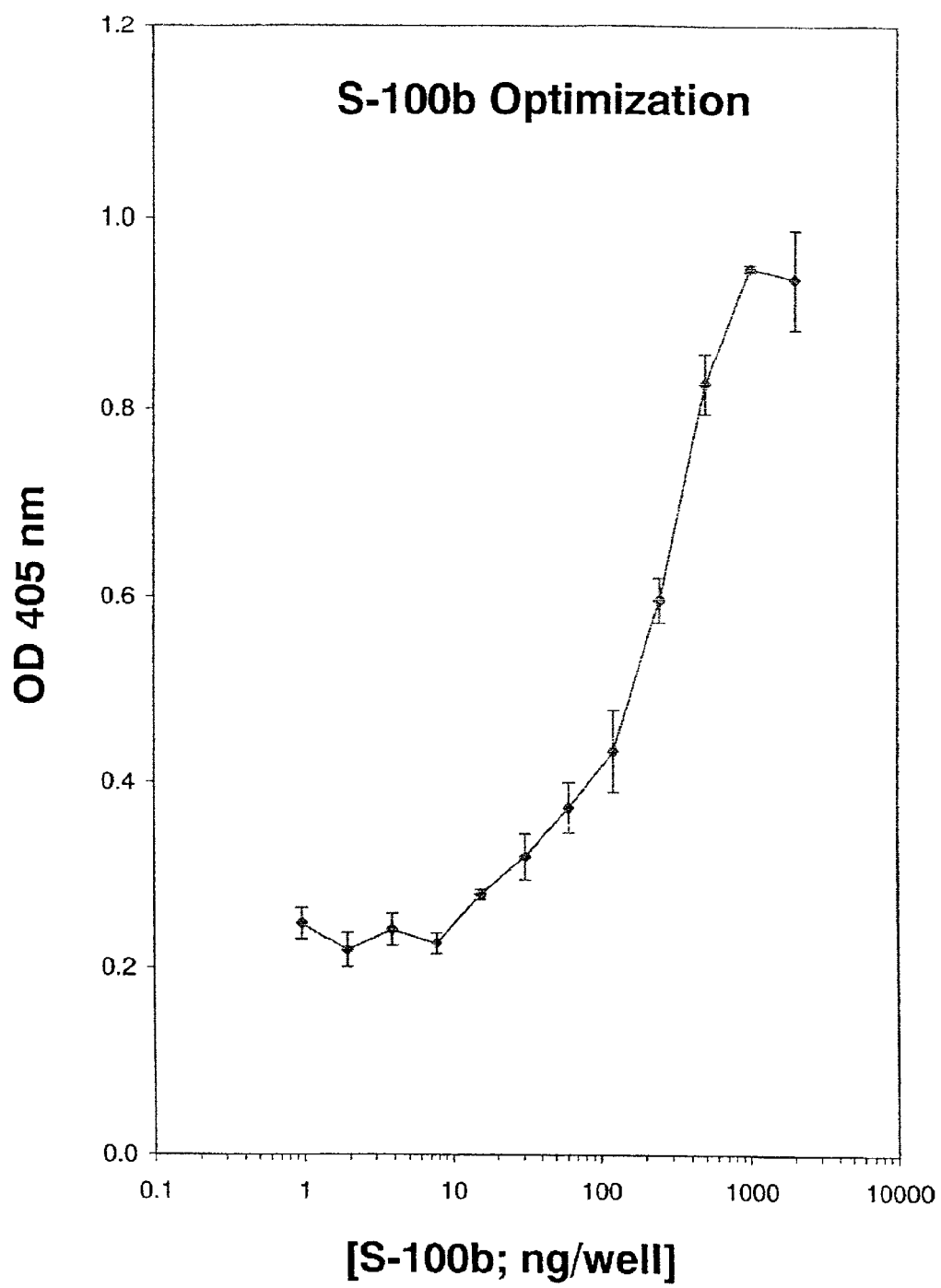
FIG. 3 shows an aspect of an embodiment of the present invention comprising optimization of S-100b concentration where sRAGE was present at $1.0 \times 10^{-4}$ mg/ml, polyclonal antibody to sRAGE was present at $3.0 \times 10^{-3}$ mg/ml, and overnight incubations were done using S-100b at concentrations which ranged from about 2 ng/well to 4 mg/well.

Experiments detailing the approach used for optimization of assay conditions are shown in FIGS. 3–6. For example, an experiment showing optimization of the assay for varying ligand concentrations is shown in FIG. 3. Thus, using sRAGE at a concentration of $1.0 \times 10^{-4}$ mg/ml FAC and polyclonal or monoclonal antibody ($3.0 \times 10^{-3}$ mg/ml and $1.9 \times 10^4$ mg/ml FAC respectively), it was found that maximal signal (1.06 OD) was achieved when S-100b at 500 ng/well was used for coating, and that ligand concentrations between 10 to 500 ng/well comprised a linear increase in sRAGE binding.

Experiments showing optimization of the assay at varying sRAGE concentrations are shown in FIG. 4. Using 500 ng/well S-100b to coat the wells, anti-sRAGE polyclonal or monoclonal antibody ($3.0 \times 10^{-3}$ mg/ml and $1.9 \times 10^{-4}$ mg/ml FAC respectively), and sRAGE ranging from 2 to 10 nM FAC, maximum signal is seen at about 10 nM sRAGE (FIG. 4).

Figure 5:
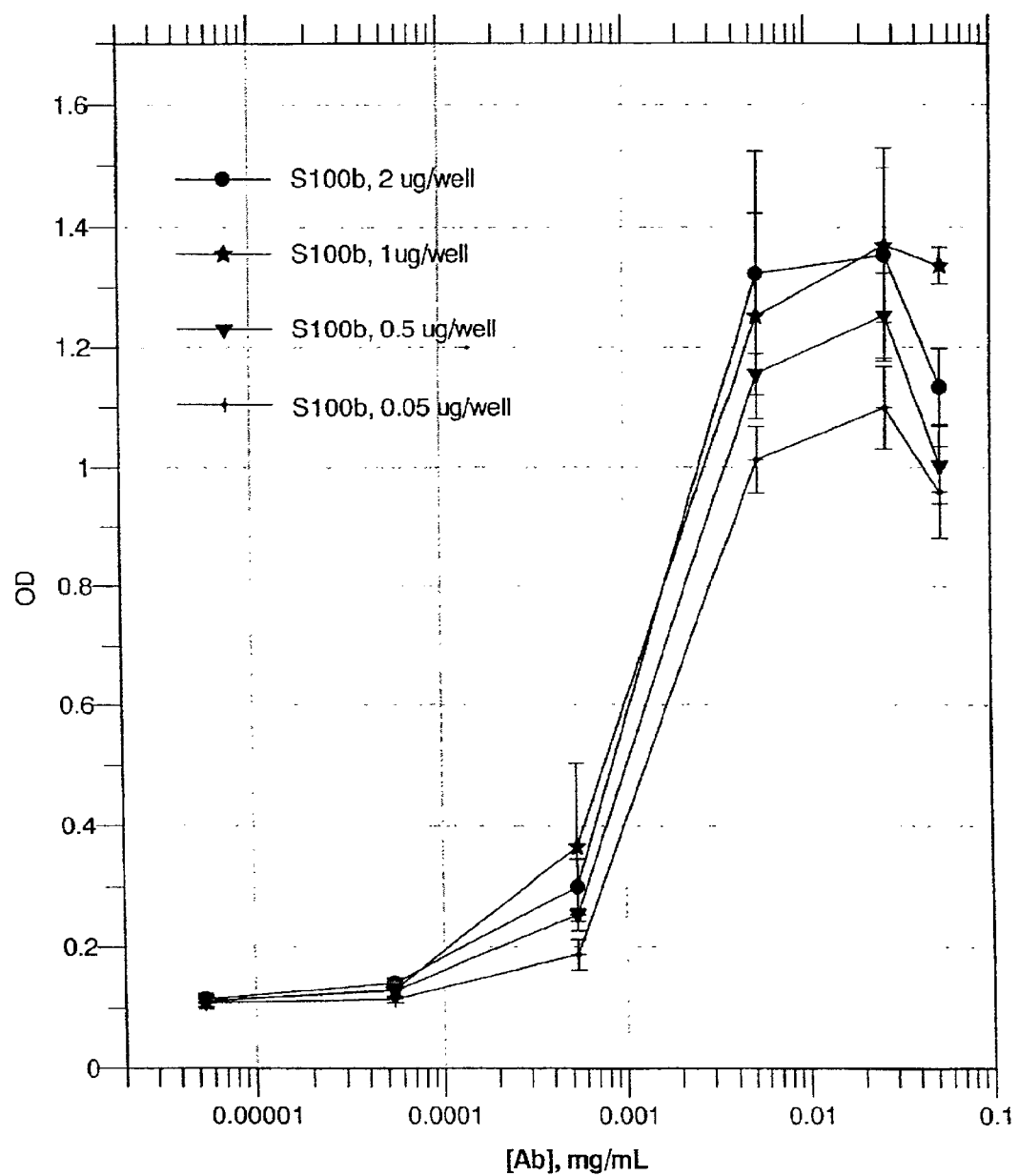
FIG. 5 shows an aspect of an embodiment of the present invention comprising optimization of antibody concentration where sRAGE was present at $1.0 \times 10^{-4}$ mg/ml, incubations were done using S-100b at 50, 500, 1,000 and 2,000 ng/well as indicated, and polyclonal antibody concentration ranged from $5 \times 10^{-6}$ to 0.054 mg/ml.

Experiments showing optimization of the assay for varying antibody concentration are shown in FIG. 5. Wells were coated using S-100b at either 50, 500, 1,000 or 2,000 ng/well overnight as indicated. sRAGE at 6 nM was added and after 1 hour at 37° C., polyclonal antibody to sRAGE comprising final concentrations ranging from $5.0 \times 10^{-2}$ to $5.5 \times 10^{-5}$ mg/ml was added. It can be seen that regardless of the concentration of ligand used to coat the wells, maximal signal was obtained at $5.4 \times 10{-3}$ mg/ml antibody. Using 500 ng/well S-100b to coat the wells, and sRAGE at $1.0 \times 10^{-4}$ mg/ml, maximal signal was found at $1.4 \times 10^{-2}$ mg/ml antibody.

Figure 6:
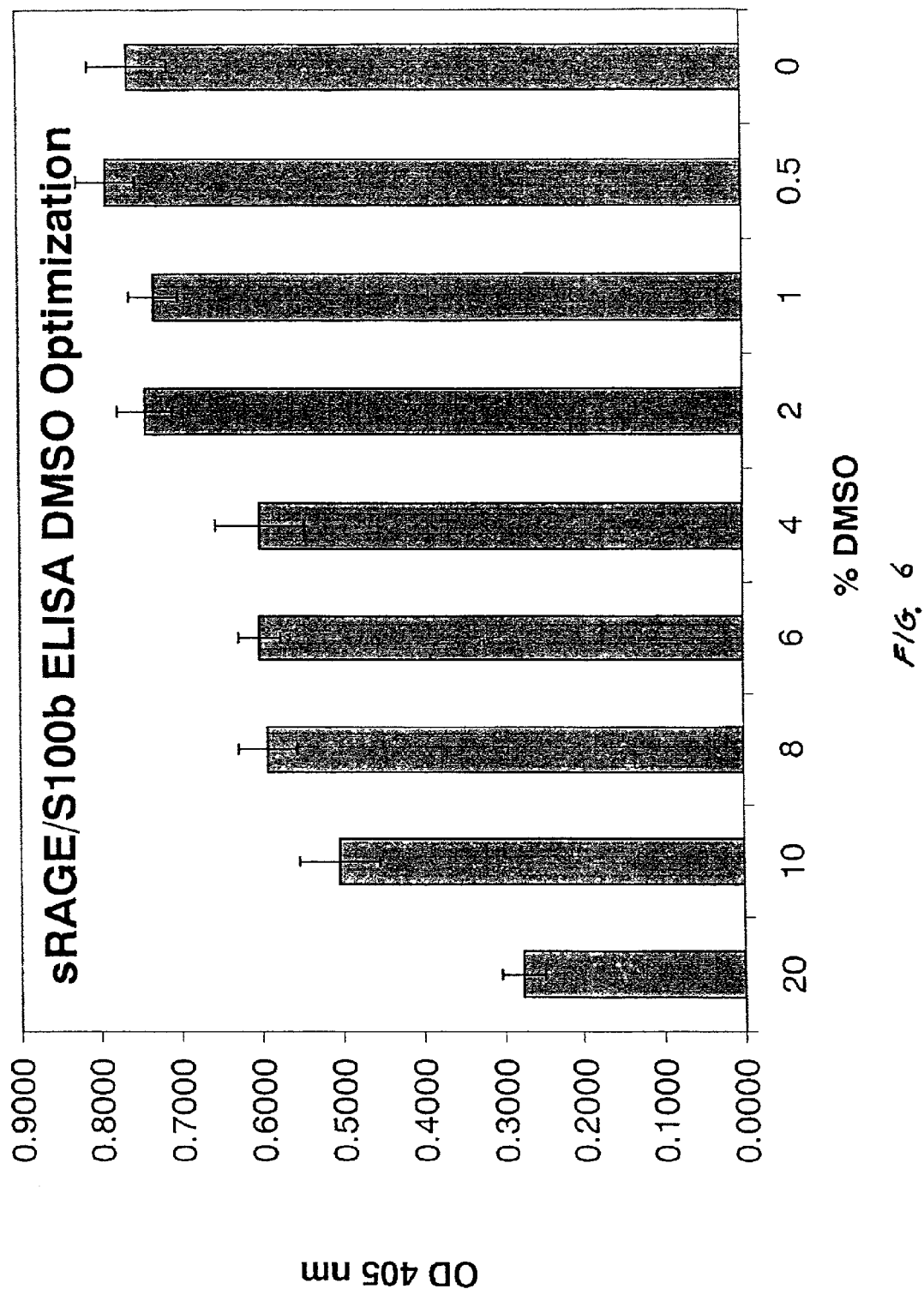
FIG. 6 shows an aspect of an embodiment of the present invention comprising optimization of DMSO tolerance where 500 ng/well S-100b was used to coat wells, and polyclonal or monoclonal antibody to sRAGE was present at $3.0 \times 10^{-3}$ mg/ml and $1.9 \times 10^{-4}$ mg/ml respectively, and the concentration of sRAGE was $2.2 \times 10^{-4}$ mg/ml.

An experiment showing optimization of the assay for varying DMSO concentrations is shown in FIG. 6. Thus, using sRAGE at a concentration of 6 nM FAC and polyclonal or monoclonal antibody ($3.0 \times 10^{-3}$ mg/ml and $1.9 \times 10^{-4}$ mg/ml FAC, respectively), it was found that maximal signal was achieved using DMSO concentrations between 0% to 2% FAC.

Example 3

Accuracy and Precision of the Assay

Figure 10:
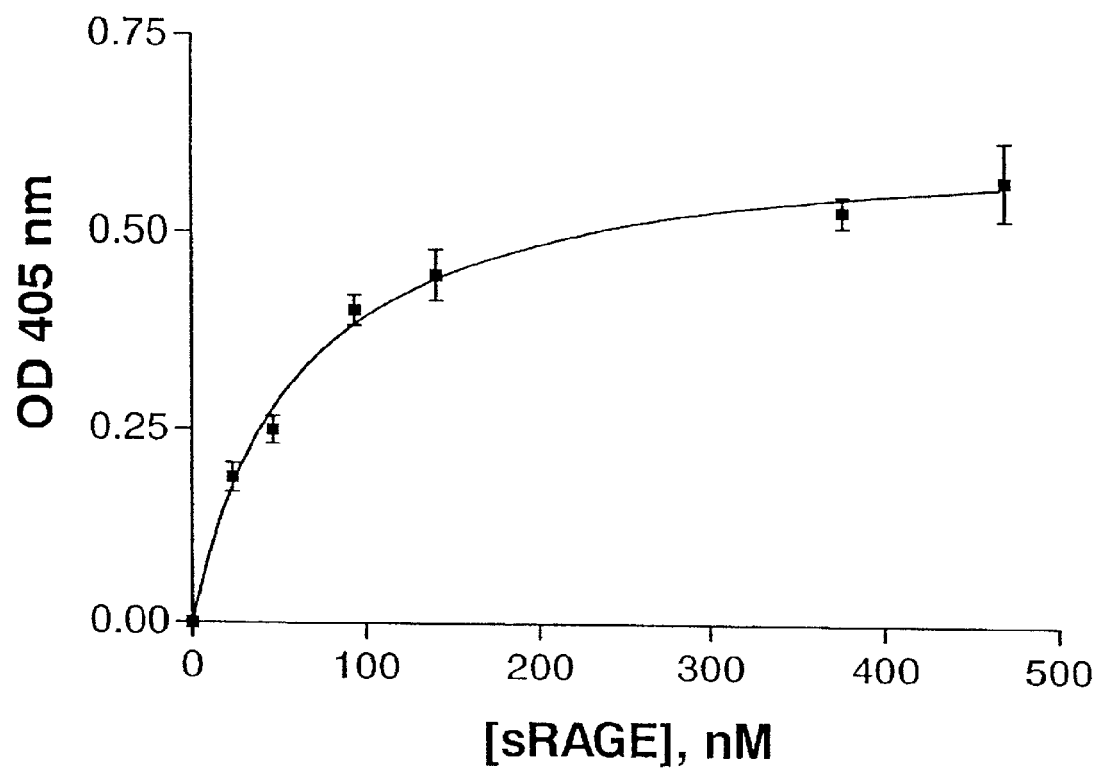
FIG. 10 shows an aspect of an embodiment of the present invention comprising a saturation curve for sRAGE binding to S-100b, where 500 ng/well S-100b was used to coat the wells, and polyclonal antibody to sRAGE was present at $3.0 \times 10^{-3}$ mg/ml, and sRAGE concentration ranged from about 24 to 470 nM.

In the experiment shown in FIG. 10, wells were coated by incubation with 500 ng/well S-100b overnight, and after washing, sRAGE diluted in buffer D added to the final concentrations shown. Polyclonal anti-sRAGE antibody ($3.0 \times 10^{-3}$ mg/ml FAC) was then added, and after 1 hr at 37° C., the plates washed and developed as described in Example 1. It was found that over four separate determinations, the goodness of fit comprised an $R^2$ of 0.9383, with Kd value of 60 and 95% confidence interval of 41.2 to 78.6.

An assessment of signal variability is shown in FIG. 7. In this experiment, 88 wells were coated by incubation with 500 ng/well S-100b overnight, and after washing, sRAGE diluted in buffer D added to all the wells with a final concentration of $2.2 \times 10^{-4}$ mg/ml. Polyclonal anti-sRAGE antibody ($3.0 \times 10^{-3}$ mg/ml FAC) was then added, and after 1 hr at 37° C., the plates washed and developed as described in Example 1. An average $OD_{405}$ of 0.705±0.054 and percent coefficient variance of 7.7 was observed. Data indicates that the signal variability from well to well is lower than 10%.

Example 4

Detection of Low and High Affinity Binding of Ligands to sRAGE

The utility of the assay for detecting compounds which antagonize both low and high affinity RAGE binding domains is shown in FIGS. 8–11. In these experiments, wells were coated with varying amounts of S-100b (50–500 ng/well overnight) and sRAGE added to each well. The amount of sRAGE bound to the immobilized ligand was detected using anti-sRAGE polyclonal or monoclonal antibody ($3.0 \times 10^{-3}$ mg/ml and $1.9 \times 10^{-4}$ mg/ml FAC, respectively) and the development system as described in Example 1. Plots were linearized by means of Scatchard analysis and values for Kd and Bmax determined. Statistical analysis of experimental precision was determined by utilizing GraghPad Prisam version 3 software (GraphPad Software, Inc. San Diego, Calif.).

Both low and high affinity binding of sRAGE to S-100b are detected using the assay method of the invention. In the experiments shown in FIGS. 8 and 9, plates were incubated overnight with S-100b at a concentration of 50 and 100 ng/well, respectively. After washing, sRAGE comprising a final concentration ranging from about 0.3 to 10 nM was added to each well, and after 1 hour at 37° C., bound sRAGE was measured by the addition of polyclonal antibody complex. For both experiments, a high affinity binding component comprising a Kd of about 6 nM (FIG. 8) to 2 nM (FIG. 9) is detected.

Figure 11:
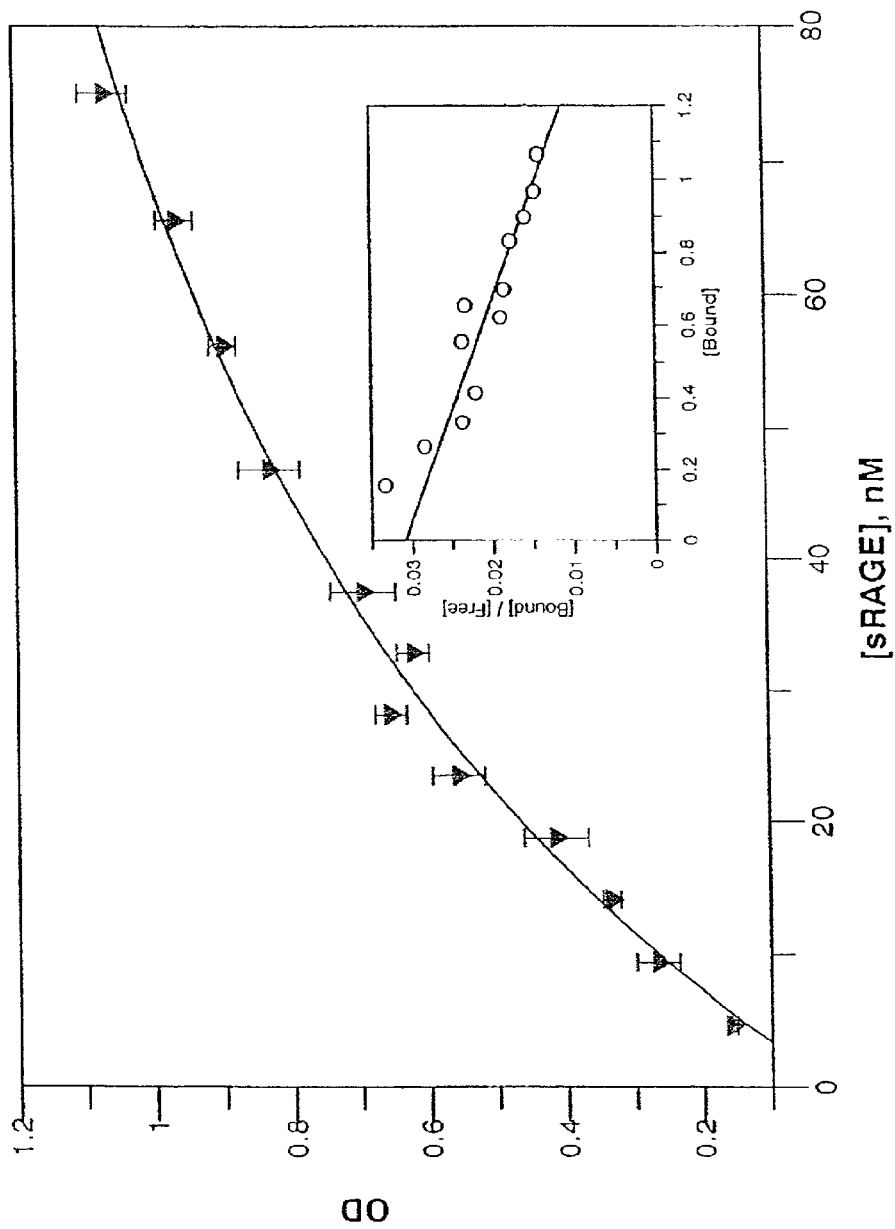
FIG. 11 shows an aspect of an embodiment of the present invention comprising a saturation curve for sRAGE binding to S-100b, where 100 ng/well S-100b was used to coat the wells, and polyclonal antibody to sRAGE was present at $3.0 \times 10^{-3}$ mg/ml, and sRAGE concentration ranged from about 5 to 76 nM.

In the experiments shown in FIGS. 10 and 11, plates were incubated overnight with S-100b at a concentration of 500 and 100 ng/well, respectively. After washing, sRAGE comprising a final concentration ranging from about 23 to 470, or 5 to 76 nM, respectively, was added to each well, and after 1 hour at 37° C., bound sRAGE measured by addition of the sRAGE polyclonal antibody complex (anti-sRAGE:IgG:streptavidin-alkaline phosphatase) and detection reagents. For both experiments, a low affinity binding site, having a Kd of about 60 nM, was detected.

Example 5

Inhibition of sRAGE Binding by Modulators

Interaction of AGE's with RAGE generates intracellular oxidative stress (Yan, et al., *J. Biol. Chem.*, 269:9889–9897 (1994)) resulting in the activation of the free radical-sensitive transcription factor NF-κB and the activation of NF-κB regulated genes (Yan, et al., *J. Biol. Chem.*, 269:9889–9897 (1994); Wautier, et al., *Proc. Natl. Acad. Sci.*, 91:7742–7746 (1994)). Since RAGE transcription is also regulated by interaction at two different NF-κB binding sites in the RAGE promoter sequence (Li, et al., *J. Biol. Chem.*, 272:16498–16506 (1997)) an ascending detrimental spiral is fueled by this positive feedback loop. A secondary cell based functional assay was used to evaluate small molecules which modulate binding of sRAGE to an immobilized ligand. The pNF-κB-Luc gene was introduced into a C6 glioma cell line expressing high levels of RAGE (see e.g. Huttunen et al., *J. Biol. Chem.*, 274:19919–24 (1999)) by transfection using standard techniques. The pNF-κB-Luc reporter is designed such that upon activation of the NF-κB, the luciferase gene is expressed. Luciferase activity is then quantified by measuring luminescence with a luminometer. Generally, expression of the luciferase gene is low. Upon introduction of a RAGE ligand, however, RAGE activates NF-κB, resulting in an increase in luciferase expression.

Thus, the assay measures the ability of a compound to modulate RAGE induced-luciferase activity. If the modulator comprises an agonist, the compound induces activation of NF-κB transcription, and luciferase activity is increased. If the modulator is an antagonist, the compound inhibits the ability of RAGE agonists to induce activation of NF-κB transcription, and luciferase activity is increased.

Figure 14:
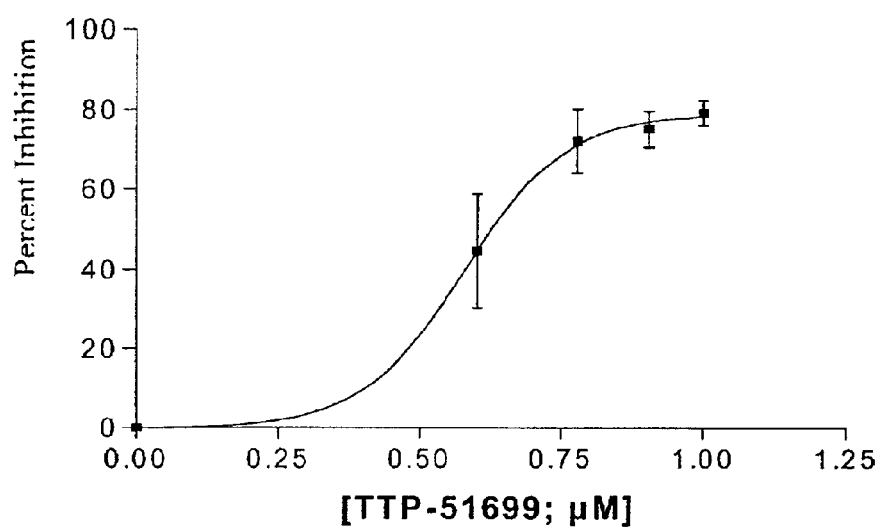
FIG. 14 shows an aspect of an embodiment of the present invention comprising an inhibition of sRAGE activation of the transcription factor NF-κB by Compound 1.

In the experiment shown in FIG. 14, inhibition of S-100b/RAGE interaction in C6 glioma cells by Compound 1 (FIG. 13) had an $IC_{50}$ of 3.3 μM. Thus, the cell based assay shown in FIG. 14 showed good correlation with the binding ELISA $IC_{50}$ value for inhibition of sRAGE binding for Compound 1 of 1.8 FM (FIG. 12).

With respect to the descriptions set forth above, optimum dimensional relationship of parts of the invention (to include variations in specific components and manner of use) are deemed readily apparent and obvious to those skilled in the art, and all equivalent relationships to those illustrated in the drawings and described in the specification are intended to be encompassed herein. The foregoing is considered as illustrative only of the principal of the invention. Since numerous modifications and changes will readily occur to those skilled in the art, it is not intended to limit the invention to the exact embodiments shown and described, and all suitable modifications and equivalents falling within the scope of the appended claims are deemed within the present inventive concept.

It is to be further understood that the phraseology and terminology employed herein are for the purpose of description and are not to be regarded as limiting. Those skilled in the art will appreciate that the conception on which this disclosure is based may readily be used as a basis for designing the methods and systems for carrying out the several purposes of the present invention. The claims are regarded as including such equivalent constructions so long as they do not depart from the spirit and scope of the present invention.

What is claimed is:

1. A method for detection of RAGE ligands comprising:
   adsorbing a RAGE ligand onto a solid surface;
   adding a compound of interest and a protein comprising sRAGE as defined by the amino acid sequence SEQ ID NO: 2, to the preadsorbed ligand;
   adding anti-RAGE antibody which binds to the sRAGE protein;
   determining the amount of sRAGE protein bound to the ligand by measuring the amount of anti-RAGE antibody bound; and
   comparing the amount of sRAGE protein bound to the ligand in the presence of varying amounts of the compound of interest.

2. The method of claim 1, wherein the anti-RAGE antibody comprises a monoclonal antibody.

3. The method of claim 1, herein the anti-RAGE antibody comprises a polyclonal antibody.

4. The method of claim 1, further comprising adding a second antibody which recognizes the anti-RAGE antibody.

5. The method of claim 4, wherein the anti-RAGE antibody and secondary antibody are allowed to complex prior to being added.

6. The method of claim 4, further comprising performing a calorimetric assay for the secondary antibody.

7. The method of claim 1, wherein the solid surface comprises a microtiter well.

8. The method of claim 1, wherein the solid surface comprises a dip-stick.

9. The method of claim 1, wherein the ligand comprises S100b.

10. The method of claim 1, wherein the compound of interest comprises a synthetic peptide.

11. The method of claim 1, wherein the compound of interest comprises a peptidomimetic.

12. The method of claim 1, wherein the compound of interest comprises an organic compound.

13. The method of claim 1, wherein the compound of interest comprises an inorganic compound.

14. The method of claim 1, wherein the compound of interest comprises a lipid.

15. The method of claim 1, wherein the compound of interest comprises a carbohydrate.

16. The method of claim 1, wherein compound of interest comprises a nucleic acid.

17. A method for detection of RAGE ligands comprising:
    adsorbing a RAGE ligand onto a solid surface;
    adding a compound of interest and a protein comprising RAGE as defined by the amino acid sequence SEQ ID NO: 2 to the preabsorbed ligand;
    adding anti-RAGE antibody which binds to the sRAGE protein and a secondary antibody which binds to the anti-RAGE antibody;
    measuring the secondary antibody bound to the anti-RAGE antibody; and
    comparing the amount of sRAGE protein bound to the ligand in the presence of varying amounts of the compound of interest.

18. The method of claim 17, further comprising performing a calorimetric assay for the secondary antibody.

19. The method of claim 17, wherein the anti-RAGE antibody and secondary antibody are allowed to complex prior to being added to the reaction.

20. The method of claims 17, wherein the solid surface comprises a reaction vessel.

21. The method of claim 17, wherein the solid surface comprises a dip-stick.

* * * * *

UNITED STATES PATENT AND TRADEMARK OFFICE
CERTIFICATE OF CORRECTION

PATENT NO. : 6,908,741 B1
APPLICATION NO. : 09/799152
DATED : June 21, 2005
INVENTOR(S) : Manouchehr M. Shahbaz It is certified that error appears in the above-identified patent and that said Letters Patent is hereby corrected as shown below:

On the tite page item (57), line 1, under Abstract, the portion reading "are methods to detect of modulators of the receptor" should read --are methods to detect modulators of the receptor--

On the title page, item (56), under Other Publications, the name "Hoffman" should read --Hofmann--

Title page under item (56), Page 3, Column 1, Line 4, the portion reading "269:9889-9887, (1994)" should read --269:9889-9897, (1994)--

Column 1, Line 34, the word "neurosis" should read --neurons--

Column 1, Line 56, the word "Hoffman" should read --Hofmann--

Column 3, Line 30, the word "apart" should read --a part--

Column 5, Line 24, the word "calorimetric" should read --colorimetric--

Column 5, Line 16, the word "NF-YB" should read --NF-κB--

Column 7, Lines 9 and 10, the word "calorimetric" should read --colorimetric--

Column 8, Line 4, the word "calorimetric" should read --colorimetric--

Column 8, Line 7, the word "fall" should read --full--

Column 8, Line 17, the portion reading "ark et al., Nature Med.," should read --Park et al., Nature Med.,--

Column 9, Line 27, the portion reading "binds in a saturable manner to S-000b" should read --binds to a saturable manner to S-100b--

Column 9, Line 51, the word "ato" should read --to--

Column 9, Line 67, the word "calorimetric.:" should read --colorimetric.:--

Column 11, Line 62, the portion reading "and Pyorala et al., Diaib. Metab. Rev.," should read --and Pyorala et al., Diab. Metab. Rev.--

Column 11, Line 64, the word "his" should read --has--

UNITED STATES PATENT AND TRADEMARK OFFICE
CERTIFICATE OF CORRECTION

PATENT NO.         : 6,908,741 B1
APPLICATION NO. : 09/799152
DATED              : June 21, 2005
INVENTOR(S)       : Manouchehr M. Shahbaz It is certified that error appears in the above-identified patent and that said Letters Patent is hereby corrected as shown below:

Column 12, Line 24, the portion reading "6:643651 (2000)" should read --6:643-651 (2000)--

Column 13, Line 12, the portion reading "Yan et (al., J. Biol. Chem.," should read--Yan et al., J. Biol. Chem--

Column 13, Line 23, the portion reading "(Wingard et al. 2001)" should read--(Chitaley et al. 2001)--

Column 13, Line 26, the portion reading "Thus, inhibiting activity ation of" should read --Thus, inhibiting activation of--

Column 18, Line 13, the portion reading "1 of 1.8 FM (Fig. 12)" should read--1 of 1.8 µM (Fig. 12).--

Column 23, Line 34, the word "herein" should read --wherein--

Column 23, Line 42, the word "calorimetric" should read--colorimetric--

Column 24, Line 31, the word "RAGE" should read --sRAGE--

Column 24, Line 42, the word "calorimetric" should read--colorimetric--

Signed and Sealed this

Sixteenth Day of January, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 404
<212> TYPE: PRT
<213> ORGANISM: Homo sapiens

<400> SEQUENCE: 1

Gly Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn

-continued

```
                100                 105                 110
Tyr Arg Val Arg Val Tyr Gln Ile Pro Gly Lys Pro Glu Ile Val Asp
            115                 120                 125
Ser Ala Ser Glu Leu Thr Ala Gly Val Pro Asn Lys Val Gly Thr Cys
        130                 135                 140
Val Ser Glu Gly Ser Tyr Pro Ala Gly Thr Leu Ser Trp His Leu Asp
145                 150                 155                 160
Gly Lys Pro Leu Val Pro Asn Glu Lys Gly Val Ser Val Lys Glu Gln
                165                 170                 175
Thr Arg Arg His Pro Glu Thr Gly Leu Phe Thr Leu Gln Ser Glu Leu
            180                 185                 190
Met Val Thr Pro Ala Arg Gly Gly Asp Pro Arg Pro Thr Phe Ser Cys
        195                 200                 205
Ser Phe Ser Pro Gly Leu Pro Arg His Arg Ala Leu Arg Thr Ala Pro
210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
        275                 280                 285
Pro Glu Ile Gly Pro Gln Asp Gln Gly Thr Tyr Ser Cys Val Ala Thr
    290                 295                 300
His Ser Ser His Gly Pro Gln Glu Ser Arg Ala Val Ser Ile Ser Ile
305                 310                 315                 320
Ile Glu Pro Gly Glu Glu Gly Pro Thr Ala Gly Ser Val Gly Gly Ser
                325                 330                 335
Gly Leu Gly Thr Leu Ala Leu Ala Leu Gly Ile Leu Gly Gly Leu Gly
            340                 345                 350
Thr Ala Ala Leu Leu Ile Gly Val Ile Leu Trp Gln Arg Arg Gln Arg
        355                 360                 365
Arg Gly Glu Glu Arg Lys Ala Pro Glu Asn Gln Glu Glu Glu Glu Glu
    370                 375                 380
Arg Ala Glu Leu Asn Gln Ser Glu Glu Pro Glu Ala Gly Glu Ser Ser
385                 390                 395                 400
Thr Gly Gly Pro

<210> SEQ ID NO 2
<211> LENGTH: 339
<212> TYPE: PRT
<213> ORGANISM: Homo sapiens

<400> SEQUENCE: 2

Gly Ala Ala Gly Thr Ala Val Gly Ala Trp Val Leu Val Leu Ser Leu
1               5                   10                  15
Trp Gly Ala Val Val Gly Ala Gln Asn Ile Thr Ala Arg Ile Gly Glu
            20                  25                  30
Pro Leu Val Leu Lys Cys Lys Gly Ala Pro Lys Lys Pro Pro Gln Arg
        35                  40                  45
Leu Glu Trp Lys Leu Asn Thr Gly Arg Thr Glu Ala Trp Lys Val Leu
    50                  55                  60
Ser Pro Gln Gly Gly Gly Pro Trp Asp Ser Val Ala Arg Val Leu Pro
```

-continued

```
                65                  70                  75                  80
Asn Gly Ser Leu Phe Leu Pro Ala Val Gly Ile Gln Asp Glu Gly Ile
                        85                  90                  95

Phe Arg Cys Gln Ala Met Asn Arg Asn Gly Lys Glu Thr Lys Ser Asn
                100                 105                 110

Tyr Arg Val Arg Val Tyr Gln Ile Pro Gly Lys Pro Glu Ile Val Asp
            115                 120                 125

Ser Ala Ser Glu Leu Thr Ala Gly Val Pro Asn Lys Val Gly Thr Cys
        130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
                180                 185                 190

Met Val Thr Pro Ala Arg Gly Gly Asp Pro Arg Pro Thr Phe Ser Cys
            195                 200                 205

Ser Phe Ser Pro Gly Leu Pro Arg His Arg Ala Leu Arg Thr Ala Pro
        210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
                260                 265                 270

Lys Asp Gly Val Pro Leu Pro Leu Pro Pro Ser Pro Val Leu Ile Leu
            275                 280                 285

Pro Glu Ile Gly Pro Gln Asp Gln Gly Thr Tyr Ser Cys Val Ala Thr
        290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335
Gly Leu Gly

<210> SEQ ID NO 3
<211> LENGTH: 112
<212> TYPE: PRT
<213> ORGANISM: Homo sapiens

<400> SEQUENCE: 3

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110
```

```
<210> SEQ ID NO 4
<211> LENGTH: 30
<212> TYPE: PRT
<213> ORGANISM: Homo sapiens

<400> SEQUENCE: 4

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20                  25                  30
```